United States Patent [19]
Russo et al.

[11] Patent Number: 6,159,735
[45] Date of Patent: *Dec. 12, 2000

[54] CALCITONIN/CALCITONIN GENE RELATED PEPTIDE ENHANCER ELEMENT AND ASSOCIATED DNA BINDING PROTEINS

[75] Inventors: Andrew F. Russo; Thomas M. Lanigan; Lois A. Tverberg, all of Iowa City, Iowa

[73] Assignee: University of Iowa Research Foundation, Iowa City, Iowa

[ * ] Notice: This patent issued on a continued prosecution application filed under 37 CFR 1.53(d), and is subject to the twenty year patent term provisions of 35 U.S.C. 154(a)(2).

[21] Appl. No.: 08/457,996

[22] Filed: Jun. 1, 1995

Related U.S. Application Data

[62] Division of application No. 08/117,364, Sep. 3, 1993, Pat. No. 5,569,604.

[51] Int. Cl.[7] ............................. C12N 15/63; C07H 21/04
[52] U.S. Cl. ........................................... 435/455; 536/24.1
[58] Field of Search ............................... 435/69.1, 172.3, 435/455, 471; 536/24.1; 935/33, 34, 36

[56] References Cited

PUBLICATIONS

Mulligan (1993) The basic science of gene therapy. Science 260:926–932, May 1993.
Coghlan (1995) Gene dream fades away. New Scientist 148:14–15, Nov. 1995.
Brown (1995) Gene therapy 'oversold' by researchers, journalists. Washington Post, Dec. 8:A22.
Peleg (1993) Down–regulation of calcitonin gene transcription by vitamin D requires two widely separated enhancer sequences. Mol. Endocrinol. 7:999–1008.
Ausubel, *Short Protocols in Molecular Biology*, 2nd ed., unit. 1.7–1.8, (John Wiley & Sons., NY 1992), pp. 1–20 to 1–27.
Besnard, P., et al., (1989) "Additive effects of dexamethasone and calcium on the calcitonin mRNA level in adrenalectomized rats", *FEBS Letters*, vol. 258, No. 2, pp. 293–296.
Burns, D.M., et al., (1989) "A Neuroendocrine Peptide Derived from the Amino–Terminal Half of Rat Procalcitonin", *Molecular Endocrinology*, vol. 3, No. 1, pp. 140–147.
Copp, D.H., (1992) "Remembrance: Calcitonin: Discovery and Early Development", *Endocrinology*, vol. 131, No. 3, pp. 1007–1008.
Cote, G.J., and Gagel, R.F., (1986) "Dexamethasone Differentially Affects the Levels of Calcitonin and Calcitonin Gene–related Peptide mRNAs Expressed in a Human Medullary Thyroid Carcinoma Cell Line", *J. Biol. Chem.*, vol. 261, No. 33, pp. 15524–15528.
Denis–Donini, S., (1989) "Expression of dopaminergic phenotypes in the mouse olfactory bulb induced by the calcitonin gene–related peptide", *Nature*, vol. 339, pp. 701–704.

Diamond, M.I., et al., (1990) "Transcription Factor Interactions: Selectors of Positive or Negative Regulation from a Single DNA Element", *Science*, vol. 249, pp. 1266–1277.
Fontaine, B., et al., (1986) "Calcitonin gene–related peptide, a peptide present in spinal cord motoneurons, increases the number of acetylcholine receptors in primary cultures of chick embryo myotubes" *Neurosci. Lett*, vol. 71, No. 1, pp. 59–65.
Giguere, V., et al., (1987) "Identification of a receptor for the morphogen retinoic acid", *Nature*, vol. 330, pp. 624–629.
Glass, C.K., et al., (1990) "Multiple Cell Type–Specific Proteins Differentially Regulate Target Sequence Recognition by the α Retinoic Acid Receptor", *Cell*, vol. 63, pp. 729–738.
Glass, C. K., et al., (1989) "Positive and Negative Regulation of Gene Transcription by a Retinoic Acid–Thyroid Hormone Receptor Heterodimer", *Cell*, vol. 59, pp. 697–708.
Hu, Y–F., et al., (1990) "Transcription factor AP–4 contains multiple dimerization domains that regulate dimer specificity", *Genes & Development*, vol. 4, pp. 1741–1752.
Johnson, J.E., et al., (1990) "Two rat homologues of *Drosophila achaete–scute* specifically expressed in neuronal precursors", *Nature*, vol. 346, pp. 858–861.
Kristie, T.M., et al., (1989) "The octamer–binding proteins from multi–protein–DNA complexes with the HSV αTIF regulatory protein", *The EMBO Journal*, vol. 8, No. 13, pp. 4229–4238.
Leff, S.E., et al., (1986) "Complex Transcriptional Units: Diversity in Gene Expression by Alternative RNA Processing", *Annu. Rev. Biochem*, vol. 55, pp. 1091–1117.
Manglesdorf, D.J., et al., (1990) "Nuclear receptor that identifies a novel retinoic acid response pathway", *Nature*, vol. 345, pp. 224–229.
Manz, B., et al., (1983) "Methyl 17β–Carboxyester Derivatives of Natural and Synthetic Glucocorticoids: Correlation Between Receptor Binding and Inhibition of in vitro Phytohaemagglutinin–Induced Lymphocyte Blastogenesis", *J. Clin. Chem. Clin. Biochem.*, vol. 21, pp. 69–75.
Mermod, N., et al., (1988) "Enhancer binding factors AP–4 and AP–1 act in concert to activate SV40 late transcription in vitro", *Nature*, vol. 332, pp. 557–561.

(List continued on next page.)

*Primary Examiner*—Robert A. Schwartzman
*Attorney, Agent, or Firm*—Lahive & Cockfield, LLP; Elizabeth A. Hanley, Esq.; Peter C. Lauro, Esq.

[57] ABSTRACT

A DNA element which was isolated from the upstream regulatory region of the CT/CGRP gene and which exhibits cell-specific enhancement of transcription is described. The enhancer activity of the element is further regulated by members of the superfamily of steroids and retinoids which increase or decrease transcription in a cell-specific manner. Methods of gene regulation and therapeutic uses involving the DNA element are also described. Furthermore, proteins which bind to the element and regulate transcription of genes under the control of the DNA element are also described. These proteins can be used for purposes of regulation of gene expression.

18 Claims, 15 Drawing Sheets

OTHER PUBLICATIONS

Mordacq, J.C. and Linzer, D.I.H., (1989) "Co–localization of elements required for phorbol ester stimulation and glucocorticoid repression of proliferin gene expression", *Genes & Development*, vol. 3, pp. 760–769.

Muszynski, M., et al., (1983) "Glucocorticoids stimulate the production of preprocalcitonin–derived secretory peptides by a rat medullary thyroid carcinoma cell line", *J. Biol. Chem.*, vol. 258, No. 19, pp. 11678–11683.

Naveh–Many, T. and Silver, J., (1988) "Regulation of Calcitonin Gene Transcription by Vitamin D Metabolites In Vivo in the Rat", *J. Clin. Invest.*, vol. 81, pp. 270–275.

Nelson, C., et al., (1988) "Activation of Cell–Specific Expression of Rat Growth Hormone and Prolactin Genes by a Common Transcription Factor", *Science*, vol. 239, pp. 1400–1405.

Nelson, C., et al., (1990) "Pan: a transcriptional regulator that binds chymotrypsin, insulin, and AP–4 enhancer motifs", *Genes & Development*, vol. 4, pp. 1035–1043.

New, H.V., and Mudge, A.W., (1986) "Calcitonin gene–related peptide regulates muscle acetylcholine receptor synthesis" *Nature*, vol. 323, pp. 809–811.

Petkovich, M., et al., (1987) "A human retinoic acid receptor which belongs to the family of nuclear receptors", *Nature*, vol. 330, pp. 444–450.

Pressley, L. and Funder, J.W., (1975) "Glucocorticoid and Mineralocorticoid Receptor in Gut Mucosa", *Endocrinology*, vol. 97, pp. 588–596.

Ray, A., et al., (1990) "On the Mechanism for Efficient Repression of the Interleukin–6 Promoter by Glucocorticoids: Enhancer, TATA Box, and RNA Start Site (Intr Motif) Occlusion", *Mol. Cell Biolog.*, vol. 10, No. 11, pp. 5736–5741.

Rosenfeld, M.G., et al., (1984) "Alternative RNA Processing: Determining Neuronal Phenotype", *Science*, vol. 225, pp. 1315–1320.

Rosenfeld, M.G., et al., (1983) "Production of a novel neuropeptide encoded by the calcitonin gene via tissue–specific RNA processing", *Nature*, vol. 304, pp. 129–135.

Russo, A.F., et al., (1988) "Differential Regulation of the Coexpressed Calcitonin/$\alpha$–CGRP and $\beta$–CGRP Neuroendocrine Genes", *J. Biol. Chem.*, vol. 263, No. 1, pp. 5–8.

Russo, A.F., et al., (1992) "Neuronal Properties of a Thyroid C–Cell Line: Partial Repression By Dexathosone and Retinoic Acid", *Mol. Endocrinol.*, vol. 6, pp. 207–218.

Schöler, H.R., (1991) "Octamania: The POU factors in murine development", *Trends in Genet.*, vol. 7, No. 10, pp. 323–329.

Stolarsky–Fredman, L., et al., (1990), "A Tissue– Specific Enhancer in the Rat–Calcitonin GRP Gene is Active in Both Neutral and Endocrine Cell Types," *Molecular Endocrinology*, vol. 4(3), p. 497–504.

Tverberg, L.A. and Russo, A.F., (1992) "Cell–specific Glucocorticoid Repression of Calcitonin/Calcitonin Gene–related Peptide Transcription", *J. Biol. Chem.*, vol. 267, No. 25, pp. 17567–17573.

Tverberg, L.A. and Russo, A.F., (1993) "Regulation of the Calcitonin/Calcitonin Gene–related Peptide Gene by Cell-–specific Synergy between Helix–Loop–Helix and Octamer–binding Transcription Factors", *J. Biol. Chem.*, vol. 268, No. 21, pp. 15695–15693.

Yang, N., et al., (1991) "Characterization of DNA binding and retinoic acid binding properties of retinoic acid receptor", Proceedings of the National Academy of Science, vol. 87, pp. 3559–3563.

Zeytin, F.N., et al., (1987) "Calcium, Dexamethasone, and the Antiglucocorticoid RU–486 Differentially Regulate Neuropeptide Synthesis in a Rat C Cell Line", *Endocrinology*, vol. 121, No. 1, pp. 361–370.

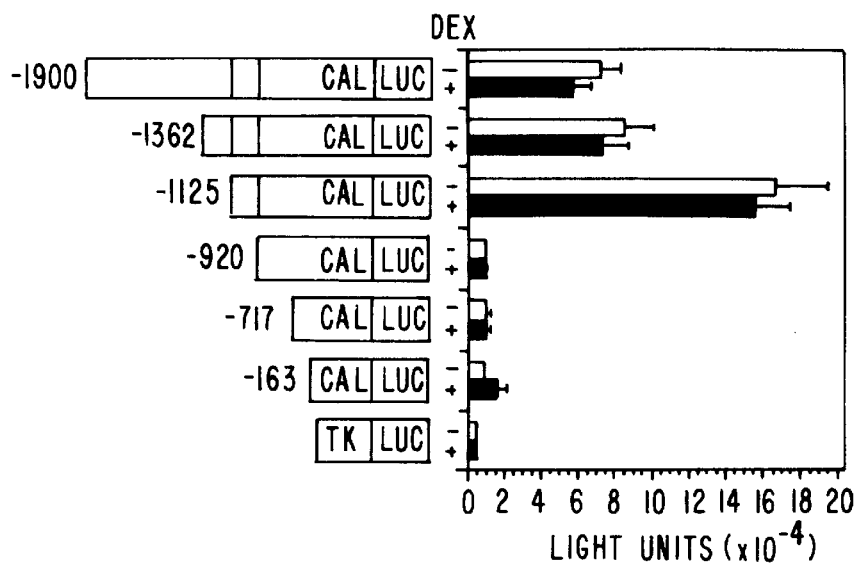
FIG. 3A
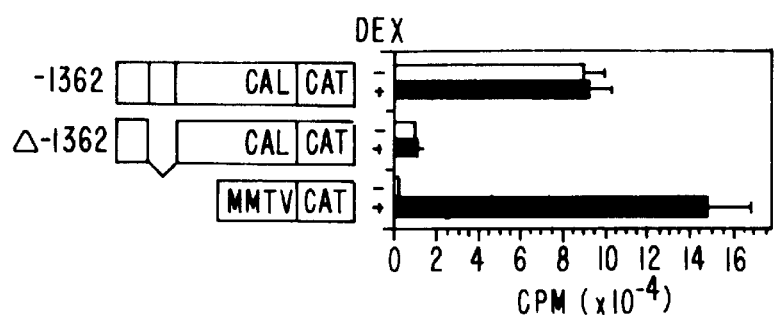
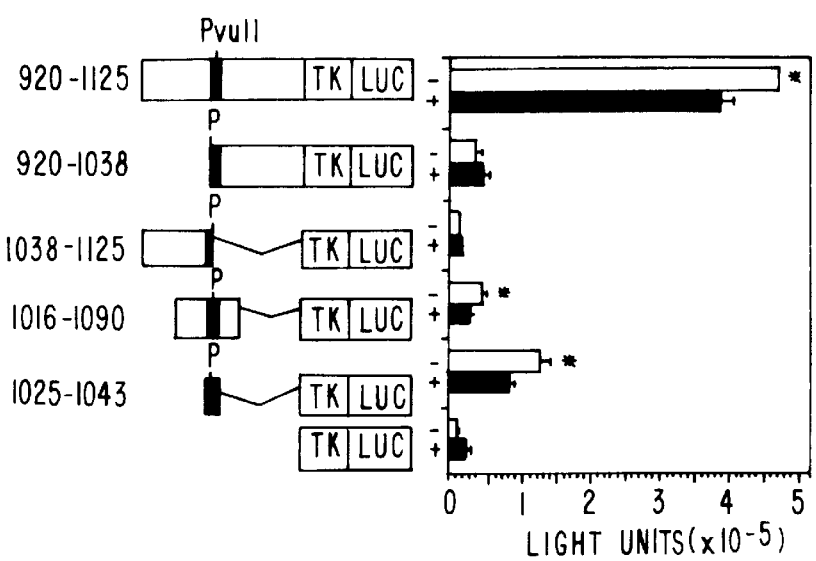
FIG. 3B

Probe

Competitor

Cell-specificity of CT/CGRP Enhancer Complexes

Model of CT/CGRP Enhancer Mechanism

FIG. IIA
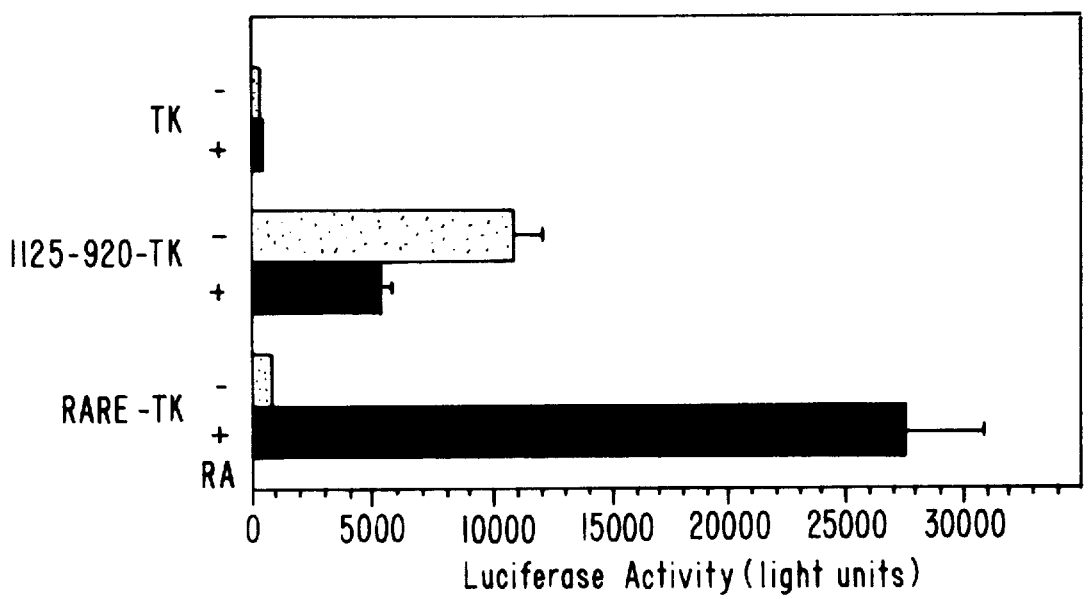
FIG. IIB
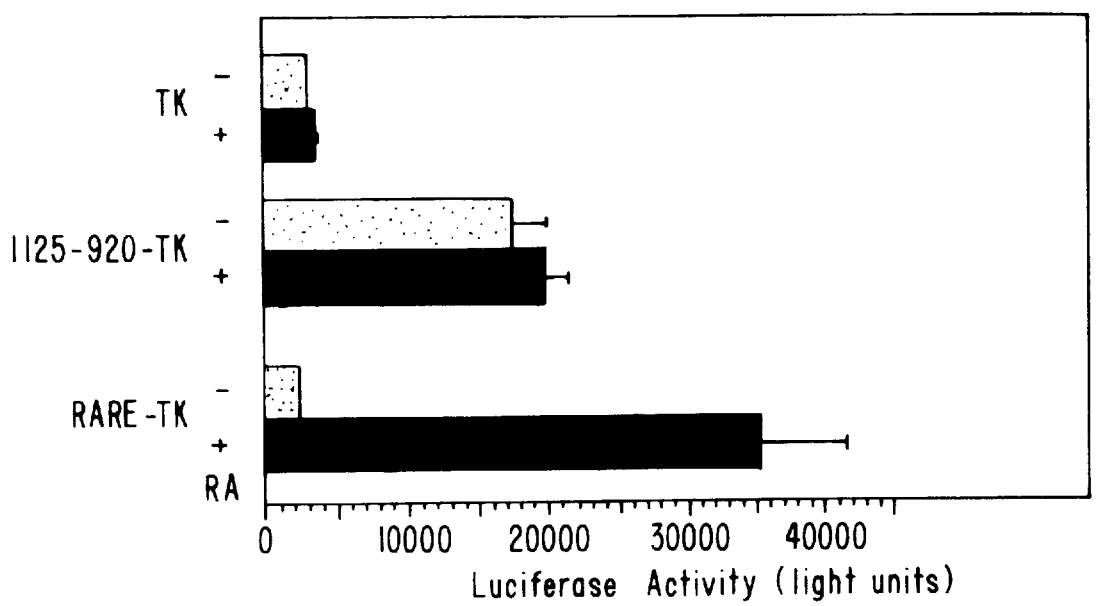

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO:1:

GGCAGCTGTG CAAATCCT                                18

(2) INFORMATION FOR SEQ ID NO:2:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: other nucleic acid (xi) SEQUENCE DESCRIPTION: SEQ ID NO:2:

GATCCGGCAG CTGTGCAAAT CCTGGATC                      28

(2) INFORMATION FOR SEQ ID NO:3:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:3:

GATCCGGACG CTGTGCAAAT CCTGGATC        28

(2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:4:

GATCCGGCAG CTGCGCAAAT CCTGGATC        28

(2) INFORMATION FOR SEQ ID NO:5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:5:

GATCCGGCAG CTGTGCAATG CCTGGATC        28

(2) INFORMATION FOR SEQ ID NO:6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:6:

GATCCGGCAG CTGTGCTGTG CAAATCCTGG ATC        33

(2) INFORMATION FOR SEQ ID NO:7:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:7:

GATCCGGCAG CTGTGCTAGA GTGTGCAAAT CCTGGATC        38

(2) INFORMATION FOR SEQ ID NO:8:

(i) SEQUENCE CHARACTERISTICS:
        (A) LENGTH: 18 base pairs (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:8:

AAGAACCAGC TGTGGAAT                                                 18

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:9:

GGCCAGAACA CCTGCAGACG                                               20

(2) INFORMATION FOR SEQ ID NO:10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:10:

GATCGAATCG AAATCACTAG CT                                            22

(2) INFORMATION FOR SEQ ID NO:11:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:11:

CCGAGCTTCA TGAATATATA TATAATCCCG A                                  31

(2) INFORMATION FOR SEQ ID NO:12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:12:

GGGTAGGGTT CACCGAAAGT TCACTCG                                       27

(2) INFORMATION FOR SEQ ID NO:13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear -continued (ii) MOLECULE TYPE: cDNA (xi) SEQUENCE DESCRIPTION: SEQ ID NO:13:

GATCCTCTAG ACATATGGGA TC                                                    22

CALCITONIN/CALCITONIN GENE RELATED PEPTIDE ENHANCER ELEMENT AND ASSOCIATED DNA BINDING PROTEINS

This application is a divisional application of Ser. No. 08/117,364 filed on Sep. 3, 1993, U.S. Pat. No. 5,569,604. The contents of all of the aforementioned application are hereby incorporated by reference.

GOVERNMENT SUPPORT

This work was supported by National Institutes of Health Grant HD25969, National Science Foundation Grant BNS8908972, and by a National Institutes of Health Grant DK25295 to the University of Iowa Diabetes and Endocrinology Research Center Tissue Culture Facility.

BACKGROUND

The calcitonin/calcitonin gene related peptide (CT/CGRP) gene is expressed in a highly cell-specific fashion in the neuroendocrine system (Rosenfeld, M. G., et al. (1983) *Nature* 304, 129–135; Rosenfeld, M. G., Amara, S. G., Evans, R. M. (1984) *Science* 225, 1315–1320). Alternative splicing leads to the selective expression of either calcitonin mRNA in thyroid C cells or the neuropeptide CGRP in central and peripheral neurons (Rosenfeld, M. G., et al. (1983). Certain members of the superfamily of steroids and retinoids confer further transcriptional regulation of the CT/CGRP gene. For example, glucocorticoid treatment increases mRNA levels of the CT/CGRP gene in rat thyroid in vivo (Besnard, P., Jousset, V., and Garel, J. M. (1989) *FEBS Lett.* 258, 293–296) as well as in human TT and rat CA77 medullary thyroid carcinoma cell lines (Cote, G. J., and Gagel, R. G. (1986) *J. Biol. Chem.* 261, 15524–15528; Muszynski, M., Bimnbaum, R. S., and Roos, B. A. (1983) *J. Biol. Chem.* 259, 11678–11683; Russo, A. R., et al. (1988) *J. Biol. Chem.* 263, 5–8). However, glucocorticoid treatment decreases expression in rat 44-2C medullary thyroid carcinoma cells (Zeytin, F. N., Rusk, S., and Leff, S. E. (1987) *Endocrinology* 121, 361–370). Vitamin D has also been shown to inhibit calcitonin/CGRP expression in vivo (Naveh-Many, T., and Silver, J. (1988) *J. Clin. Invest.* 81, 1–14).

Both Calcitonin and CGRP play important biological roles. Calcitonin acts in the regulation of bone and mineral metabolism. Therapeutic application of calcitonin prevents bone resorption and is useful in the treatment of Paget's disease, hypercalcemia and osteoporosis (*Physicians Desk Reference* (1987) Medical Economic Company, Inc., Oradell, N.J., 41$^{st}$ ed.). Furthermore, calcitonin has also been implicated in pain suppression and may have potential uses as an analgesic (Copp, D. H. (1992) *Endocrinology* 131, 1007–1008). The CORP gene product is a neurotrophic factor, a potent vasodilator, and acts in cardiovascular and gastrointestinal homeostasis (Leff, S. E., Rosenfeld, M. G., and Evans, R. M. (986) *Annu. Rev. Biochem.* 55, 1097–1117; Fontaine, B. et al. (1986) *Neurosci. Lett.* 7, 59–65; New, H. V. and Mudge, A. W. (1986) *Nature* 323, 809–811; Denis-Donini, S. (1989) *Nature* 339, 701–704).

Previous work had identified a 520 bp region of the CT/CoRP upstream regulatory region responsible for cell-specific enhancement of basal transcription (Stolarsky-Fredman, L., et al. (1990) *Mol. Endo.* 4, 497–504). However, the specific regulatory elements and transcription factors required for the highly restricted expression of the CT/CORP gene had yet to be identified.

SUMMARY OF THE INVENTION

The present invention is based, at least in part, on the discovery of an 18 bp DNA enhancer element hereinafter enhancer element) and transcription factors which are involved in the regulation of transcription of the Calcitonin/Calcitonin Gene Related Protein (CT/CORP) genes.

Isolation of the DNA elements and transcription factors allowed for the development of methods for in vivo regulation of calcitonin and CGRP as well as for cell-specific expression of other pharmacologically important gene products. The present invention pertains to the 18 bp DNA element from the upstream regulatory region of the CT/CORP gene which regulates transcription and also to the protein factors which bind the element. The present invention also pertains to recombinant expression vectors and host cells containing the enhancer element.

The present invention even further pertains to a method for regulating gene expression by selecting a gene of interest and constructing a DNA sequence containing the gene of interest and the enhancer element. The DNA construct is then inserted into a recombinant expression vector and introduced into a host cell. The host cell is maintained under conditions such that expression of the gene is regulated. The host cell can be cell in vivo or a cell in culture. For example, the enhancer element can be used to increase the yield in an in vitro protein production process.

The present invention also pertains to therapies for calcitonin- and CGRP-associated states. The methods include the expression of calcitonin under the regulation of the enhancer element for the treatment of diseases such as Paget's disease, osteoporosis, hypercalcemia, as well as in the alleviation of pain. The methods also include the regulation of CGRP gene expression for treatment of hypertension and other gene therapy uses. The methods also pertain to the use of the invention for cell specific expression of other pharmacologically active gene products.

In another aspect of the invention, the enhancer element is used to repress CT/CGRP enhancer activity. This method involves introducing oligonucleotides or vectors containing multiple copies of the enhancer element whereby these DNAs act to compete for binding of enhancer binding factors. The reduction in factor binding to the enhancer element regulating gene expression prevents activation of transcription of the gene.

The present invention also pertains to methods for selection of other compounds which have the ability to affect transcription regulation by the CT/CGRP enhancer element. These methods involve the transfection of a DNA construct containing a reporter gene and the enhancer element. These cells would be treated with the chosen compounds and assayed for the activity of the reporter gene compared to untreated cells. Agents which change the level of transcription of the reporter gene have the ability to affect transcription regulation by the CT/CGRP enhancer.

The present invention also pertains to the proteins which bind to the 18 bp element. The invention includes two protein factors, one of which binds to the site CAGCTG and is part of the complexes HLH (e.g., HB1 and HB2) formed in electrophoretic mobility shift assays with oligonucleotides containing the CT/CGRP enhancer sequence. The other factor binds to the site GTCAAAT and is part of the complex OB2. These factors are specific to the cells which exhibit transcriptional enhancement of the CT/CGRP gene, including neuroendocrine cells. This invention further pertains to homologs of the identified proteins which also bind to the enhancer element and mediate regulation of transcription.

The present invention also pertains to methods of regulating gene expression using the identified transcription factors. These methods include the direct application of the proteins to the cells or the transfection of DNA containing the genes encoding the proteins into cells to control expression of the calcitonin and CGRP gene products or any other gene of interest.

BRIEF DESCRIPTION OF THE DRAWINGS

FIGS. 3A, 3B, 3C, and 3D show assays of the activity of deletions of the CT/CGRP regulatory region in the fusion genes described in the *Materials and Methods* in CA77 (FIGS. 3A and 3B), HeLa (FIG. 3C) and Rat1 (FIG. 3D) cells. The cell extracts were assayed and normalized as described in FIG. 1. The activity of 50 µg of cell extract is shown and each bar represents the means standard deviations of at least three independent trials.

In FIG. 6A, radiolabeled oligonucleotide probes containing wild type or mutant CT/CGRP enhancer sequences were incubated with 44-2C nuclear extracts, and the complexes were resolved on a native polyacrylamide gel. The positions of the binding proteins are indicated, and the free probe is at the bottom of the autoradiograph. In FIG. 6B, 44-2C cell extracts were preincubated with 25-fold molar excess of the indicated unlabeled competitor oligonucleotide. The H/OB complex was not detectable in these autoradiograms because it co-migrates with OB1. FIG. 6C shows mobility shift assays in which 44-2C cell extracts were preincubated with no competitor (lane 1), 25-fold excess (lanes 2, 4, 6, 8, 10) or 50-fold excess (lanes 3, 5, 7, 9, 11) of the indicated unlabeled competitor oligonucleotide. The H/OB complex is indicated both on the left and right sides by an arrow.

FIG. 7A shows mobility shift assays using the CT/CGRP enhancer probe with nuclear extracts from HeLa cells or CA77 cells. For reference, a mobility shift using 44-2C cell extract is shown. Extracts were preincubated without competitor (lanes 1,2, and 5) or with 25-fold excess unlabeled CT/CGRP enhancer oligonucleotide (lane 6), AP-4 HLH oligonucleotide (lanes 3 and 7), or consensus octamer oligonucleotide (lanes 4 and 8). FIG. 7B is a summary of CT/CGRP enhancer activity and binding proteins observed in different cells. FIG. 7C presents a schematic model of the CT/CGRP enhancer activation mechanism.

In FIG. 8A, CA77 cells were transfected with luciferase fusion genes and treated with 1 µM retinoic acid (RA) (+) or the ethanol vehicle (-) for 24 hours, then assayed for luciferase activity. Fusion genes are schematically shown containing the: 5' flanking sequences of rat CT/CGRP (CAL), thymidine kinase promoter (TK), CT/CGRP cell-specific enhancer linked to the TK promoter (1125-920-TK), tandem elements of the β-RAR gene retinoic acid response element linked to the TK promoter (RARE-TK), and cytomegalovirus promoter (CMV). The means with standard deviations from 3–6 independent experiments normalized to the average activity of TK-luc are shown. The activities are reported per 50 µg extract, except CMV-luc, which is per 10 µg extract. In FIG 8B, fusion genes containing the TK promoter with the indicated fragments of the CT/CGRP enhancer region were transfected into the CA77 cells. In addition, constructs containing point mutations in the HLH and octamer motifs of the 18 bp enhancer element are indicated. The luciferase activities normalized to the average activity of TK-luc are shown from 2-3 experiments with standard deviations, except for 1043-1025-TK which is from one experiment.

In FIG. 10A, the CAL1125-luc fusion gene (5 μg) was transfected with (+) or without (−) the α-RAR expression vector (25 μg) into the CA77 cells and treated with either 1 μM retinoic acid or the ethanol vehicle control. The mean fold decrease and standard deviation relative to control activities following retinoic acid treatment from three experiments are shown. The luciferase activity of CAL1125-luc minus retinoic acid and α-RAR was at least 10,000 light units. As a control, CMV-luc activity was essentially unaffected by the cotransfected α-RAR vector as shown from a single experiment. In FIG. 10B, the RARE-TK-luc fusion gene was transfected as described in the FIG. 10A description. The fold increase in RARE-TK-luc activity following retinoic acid treatment in the presence or absence of cotransfected α-RAR expression vector is shown from a single experiment.

FIGS. 11A and 11B show a comparison of retinoic acid affects on CT/CGRP enhancer activity in 44-2C and HeLa cells. In FIG. 11A, the luciferase fusion genes were transfected into the 44-2C cells and treated with either 1 μM retinoic acid (+), or the ethanol vehicle (−). The activities are reported as the means with standard deviations (normalized to the average TK-luc activity) from 5 experiments. In FIG. 11B, the luciferase fusion genes were transfected into HeLa cells along with the α-RAR expression vector and treated with 1 μM retinoic acid (+) or ethanol vehicle (−). The activities were normalized as in FIG. 11A, from 2 experiments.

DETAILED DESCRIPTION

Figure 1A:
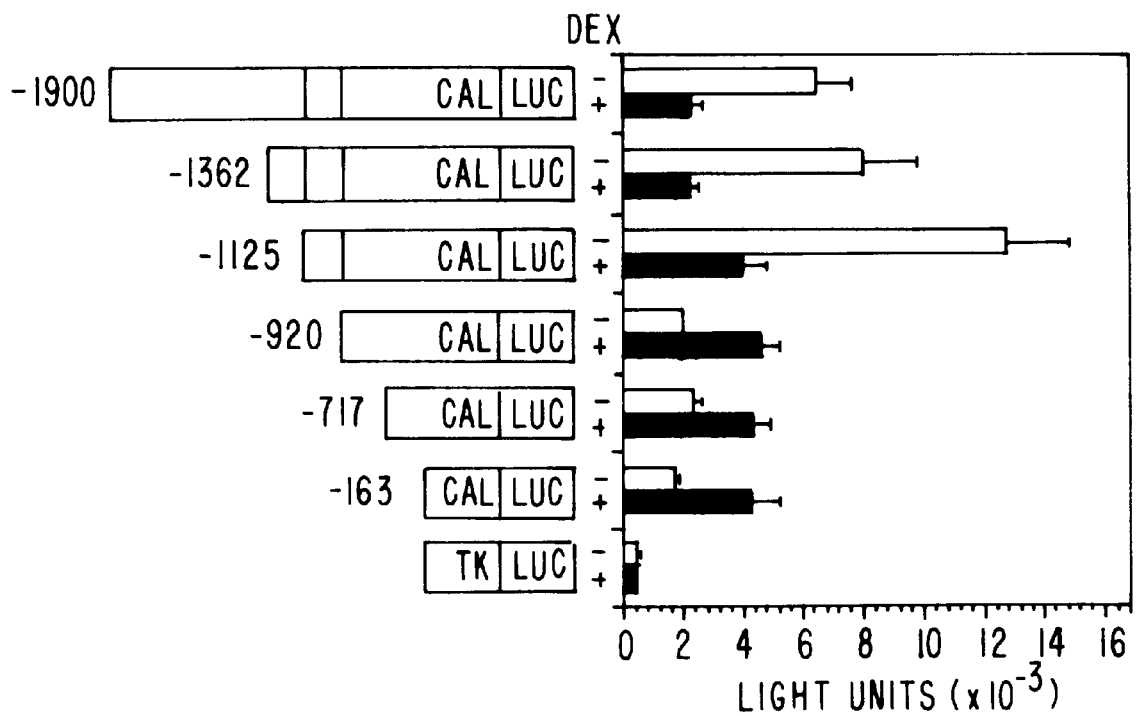
FIGS 1A, 1B and 1C show the transcriptional activity of the constructs containing deletions of the CT/CGRP upstream regulatory region as described in the *Materials and Methods*. All trials were performed by transfection into 44-2C cells and treated either with 500 nM Dexamethasone (closed bars) or the ethanol carrier alone (open bars). Cell extracts were assayed for luciferase or CAT reporter activity /50 µg of protein except for MMTV-CAT, which was with 5 µg of protein. To compensate for variations in transfection efficiencies, reporter activity was normalized to that of the -920-CAL-LUC plasmid for luciferase fusions or Δ-1362-CAL-CAT for the CAT fusions. The means and standard deviations of at least five independent experiments are shown.

The present invention pertains to purified DNA containing a sequence which regulates transcription of the Calcitonin/ Calcitonin Gene Related Protein (CT/CGRP) genes. An example of such a sequence is the enhancer element as follows: GGCAGCTGTGCAAATCCT (SEQ ID NO: 1). The sequence includes one strand of the double stranded nucleic acid present naturally in the genome. The sequence was identified as described in the examples set forth below by its ability to increase the basal level of CT/CGRP gene expression in neuroendocrine cells.

The language "purified DNA" is intended to include a piece of DNA which has been isolated at both ends from the sequences with which it is immediately contiguous in the naturally occurring genome of the organism from which the DNA of the invention is derived. The purified DNA can be an oligonucleotide which is either double or single stranded; a DNA fragment incorporated into a vector, for example an autonomously replicating plasmid or virus; a fragment inserted into the genome of a eukaryotic or prokaryotic organism; or a fragments used as a probe. The purified DNA can include the CT/CGRP enhancer sequence described above. The purified DNA can further be a sequence whose ability to regulate transcription of a gene of interest is affected by an agent from the superfamily of steroids and retinoids.

The language "regulates transcription" is intended to include a mechanism which increases or decreases the production of mRNA from a particular gene. Regulation of transcription can be measured using a promoter and upstream regulatory region fused to a gene, preferably a reporter gene whose activity is easily measured. This reporter gene could include luciferase, chloramphenicol acetyltransferase, or β-galactosidase, the assay of each of which is described in the Examples set forth below.

The language "Calcitonin/Calcitonin Gene Related Proteins" is intended to include the protein products from the Calcitonin/Calcitonin Gene Related Protein gene. These products include calcitonin and calcitonin gene related protein, the mRNAs of which are both transcribed from the same transcription unit in the organism. For purposes of this invention, the term calcitonin, alone or in combination with other words, e.g., calcitonin-associated, is intended to include proteins in the calcitonin family. Proteins in the calcitonin family include precursors to calcitonin and fragments derived from the expression or processing of the calcitonin protein, e.g., N-terminal peptide (Burns et al., *Molecular Endocrinology*, Vol. 3 p. 140–47 (1989)). The N-terminal peptide is a bone mitogen. A single mRNA is processed differentially to generate a processed mRNA which codes either for calcitonin or CGRP in a cell specific manner. Examples of functions of calcitonin include regulation of bone metabolism and blood calcium. Examples of functions of CGRP include the regulation of cardiovascular and gastrointestinal homeostasis.

The language "gene of interest" is intended to include a DNA sequence which codes for a protein product whose production can be regulated by the above described enhancer element. Examples of genes of interest include genes encoding calcitonin, CGRP, other hormones (e.g., parathyroid hormones or insulin) enzymes involved in neurochemical synthesis, e.g., tryptophan hydroxylase, (involved in serotonin synthesis).

The language "affected" is intended to include the action of the agent which either increases or decreases transcription. The agent can be selected based on its ability to achieve a desired end result, e.g. increase or decrease in transcription. Examples of agents which increase transcription include glucocorticoids in rat thyroid cells in vivo.

Examples of agents which decrease transcription include dexamethasone in 44-2C cells and retinoic acid in 44-2C and CA77 cells.

The language "agent from the super-family of steroids and retinoids" is intended to include an agent which is classified as a steroid, retinoid or related compounds (such as Vitamin D and thyroid compounds) or will bind to a receptor of the superfamily of steroid and retinoid nuclear receptors. These agents include, but are not limited to, glucocorticoids, including corticosterone and dexamethasone, retinoids, including retinoic acid and 9-cis-retinoic acid, vitamin D (e.g., 1, 25 dihydroxy vitamin D), thyroid hormones (e.g., $T_3$, $T_4$) and mineralocorticoids (aldosterone). Examples of the regulatory action of agents of the superfamily of steroids and retinoids includes their effect on the activity of the CT/CGRP enhancer. This regulatory action can be the repression of genes under the control of the CT/CGRP enhancer in 44-2C cells and by retinoic acid in CA77 cells.

The language "enhances transcription" is intended to include the mechanism of increasing the amount of mRNA production from a particular gene as compared to mRNA production from the same gene without the DNA element, DNA binding factor or agent responsible for regulating transcription.

The language "represses transcription" is intended to include the mechanism of decreasing mRNA production from a particular gene as compared to mRNA production from the same gene without the DNA element, DNA binding factor or agent responsible for regulating transcription.

The language "homolog" is intended to include a sequence similar to the DNA sequence described above which still has the ability to regulate the transcription of the CT/CGRP gene. Homologs may be screened for activity by creating mutations in the DNA sequence described above, inserting that sequence in the place of the described sequence in an expression vector containing a promoter and a gene whose activity can be measured. The expression vector can then be inserted into a cell which exhibits CT/CGRP enhancer activity. If the activity of the reporter gene is the same as the reporter gene under the control of the naturally occurring CT/CGRP enhancer then the tested sequence is a functional homolog. For example, the sequences of the oligonucleotides OctMut1, OctMut2, and HLHMut (described in the examples set forth below), which have mutations in one of the protein factor binding sites, cannot enhance the activity of the CT/CGRP gene and thus are not homologs.

The language "recombinant expression vector" is intended to include a vehicle for introducing DNA into a cell, e.g. an autonomously replicating piece of DNA such as a plasmid or a virus. The present invention also pertains to recombinant expression vectors containing the above-described enhancer element(s). The vector can contain the CT/CGRP enhancer element, a promoter such as the CT/CGRP promoter, thymidine kinase promoter or another promoter responsive to CT/CGRP enhancer regulation, and a protein coding gene such as calcitonin, CGRP, a reporter gene or some other gene of interest. The vector permits regulation of gene expression in host cells in which the enhancer and promoter elements are active.

The language "host cell" is intended to include a living cell capable of expressing a gene from the defined recombinant expression vector. The living cell includes both a cultured cell and a cell within a living organism. Examples of host cells include cells cultured from endocrine tissue or neuro-tissue. Examples of cells cultured from endocrine tissue include the rat cell lines CA77 and 44-2C which were derived from medullary thyroid carcinoma cells. Examples of neurotissue include dorsal root ganglia and neural cell lines.

The language "capable of directing expression" is intended to include the ability of the cell to express the gene contained on the recombinant expression vectors.

The language "neuroendocrine derived" is intended to include a cell which is part of the nervous or endocrine systems of an organism or is cultured from nervous or endocrine tissue.

The invention also pertains to methods for regulating the expression of the genes encoding calcitonin or CGRP or any other gene of interest, as defined above. The regulation can be in vivo or in vitro, e.g. gene therapy or production of a protein in cell culture. The method includes construction of a DNA sequence which includes the gene to be regulated, the 18 bp enhancer element, and optionally a promoter sequence. This construct is then inserted into a recombinant expression vector, as defined above, and the resulting vector is then inserted into a host cell. The method can include treatment of the cell with an agent which represses or enhances transcription from a promoter regulated by the 18 bp element. Examples of such agents can include members of the superfamily of steroids and retinoids.

The language "regulating gene expression" is intended to include the control of the production of a protein product from a gene. In this invention, regulating gene expression includes controlling the amount of mRNA transcribed from the gene under the control of the DNA element and/or expression of the gene product. The regulation can include either enhancement or repression of transcription initiation. In particular, the term refers to regulation by the presence of the CT/CGRP enhancer and/or by treatment with members of the superfamily of steroids and retinoids.

The language "DNA construct" is intended to include a DNA sequence which contains more than one individual DNA element. For example, the DNA construct can contain the gene of interest, a promoter element and the CT/CGRP enhancer element.

The language "gene of interest", "recombinant expression vector", and "host cell" are intended as defined above.

The language "inserting the recombinant expression vector into a host cell" is intended to include methods known in the art for introducing DNA into a cell. Examples of methods for introducing DNA into cell include transient transfection, by electroporation, and lipofection.

The language "conditions such that the expression of the gene of interest is regulated" is intended to include a set of conditions such that the CT/CGRP enhancer affects the transcription of the gene of interest and/or an agent of the superfamily of steroids and retinoids can regulate CT/CGRP enhancer activity. Examples of conditions under which a gene under the control of the CT/CGRP enhancer is regulated are provided in the Examples section set forth below.

The invention further pertains to a method for repressing CT/CGRP enhancer activity. This method includes the introduction of multiple copies of the CT/CORP enhancer sequence into a cell which exhibits CT/CGRP enhancer activity. These sequences can be either in the form of oligonucleotides or contained on a DNA vector separate from the vector containing the gene to be regulated. These DNA enhancer elements not in cis with the gene to be regulated compete for and reduce binding of transcription factors to the enhancer element and thereby repress enhancer activity. The language "repressing CT/CGRP enhancer activity" is intended to include methods which prevent the activation of transcription of a gene under the control of the CT/CGRP enhancer.

The language "multiple DNA sequences" is intended to include a multiple of DNA sequences which is significantly high to cause competition and reduce binding of the transcription factors to the enhancer element and thereby repress enhancer activity. As an example, more than 10 CT/CGRP enhancer sequences can be used to decrease CT/CGRP enhancer activity. The number of enhancer sequences required to be provided in trans can be determined by transfecting a certain number of sequences into a cell containing a reporter gene under the control of the CT/CGRP enhancer. The number of sequences is sufficient when the activity of the reporter gene is significantly repressed, e.g. completely. The language "oligonucleotides" is intended to include pieces of DNA of less than 40 nucleotides which contain the CT/CGRP enhancer sequence.

The invention also pertains to a method for treating a calcitonin-associated state. This method includes introducing into the subject having a calcitonin-associated state, as defined below, a DNA construct which encodes all or part of the calcitonin protein and a sequence which enhances the transcription of the calcitonin gene. The sequence can be the CT/CGRP 18 bp enhancer element. The DNA construct is introduced under conditions such that calcitonin is produced at a level which is therapeutically effective such that the state or the symptoms of the state are alleviated either partly or entirely. For example, this regulation can be carried out by the administration of an agent from the superfamily of steroids and retinoids.

The language "calcitonin-associated state" is intended to include a syndrome caused or aggravated by a lack of active calcitonin or a syndrome in which the administration of active calcitonin alleviates, in whole or in part, the state or symptoms of the state. The state can be a condition or a disease. Examples of calcitonin-associated diseases include osteoporosis, Paget's disease and hypercalcemia. Pain is an example of calcitonin-associated condition because the application of calcitonin will relieve pain in the subject.

The language "a level which is therapeutically effective" is intended to include the level of expression which produces enough of the active agent, e.g. calcitonin, to significantly reduce or alleviate the symptoms of the subject derived from the calcitonin-associated state. The therapeutically effective level of expression will vary according to factors such as the seriousness and type of disease, as well as the age, sex, and weight of the subject.

The invention also pertains to a method for treating a CGRP-associated state. This method includes introducing into the subject having a CGRP-associated state, as defined below, a DNA construct which encodes all or part of the CGRP protein and a sequence which enhances the transcription of the CGRP gene. The sequence can be the CT/CGRP 18 bp enhancer element. The DNA construct is introduced under conditions such that CGRP is produced at a level which is therapeutically effective such that the state or the symptoms of the state are alleviated either partly or entirely. For example, this regulation can be carried out by the administration of an agent from the superfamily of steroids and retinoids.

The language "CGRP-associated state" is intended to include a syndrome caused or aggravated by a lack of active CGRP or a syndrome in which the administration of active CGRP alleviates, either in whole or in part, the state or symptoms of the state. An example of a CGRP-state is the disease hypertension.

The invention also includes a method of selecting agents which regulate the CT/CGRP enhancer activity. The method includes inserting the CT/CGRP enhancer element and a reporter gene into a vector and inserting the vector into a cell, in the preferred embodiment a cultured neuroendocrine cell. The cell is then exposed to the agent suspected of affecting CT/CGRP enhancer activity, and the transcription efficiency is measured by the activity of the reporter gene. The activity can then be compared to the activity of the reporter gene in cells unexposed to the agent in question.

The language "DNA construct", "expression vector", and "host cell" is intended as defined above.

The language "reporter gene" is intended to include a gene whose protein product can be detected by a defined assay system. The assay system can include colorimetric, enzymatic, radio or immunological assays or a combination of these. Examples of reporter genes include the luciferase gene, the chloramphenicol acetyltransferase gene and the β-galactosidase gene, the assays of which are described in the Materials and Methods section set forth below.

The language "reporter gene efficiency" is intended to include a measure of the degree of expression of the gene as compared to a control. In this invention, the reporter gene efficiency is measured as the amount of reporter gene product expressed in cells treated with the selected agent as compared to the amount of product expressed in untreated cells.

The invention also includes proteins which bind to the CT/CGRP enhancer and are required for enhancer activity. The invention includes a composition which contains at least one of two such binding factors, one of which binds to the binding site CAGCTG and is part of the complex HLH (e.g. HB1 and/or HB2) and the other of which binds to the site GTGCAAAT and is part of the complex OB2. These proteins have utility in the activation of transcription of genes under the control of the CT/CGRP enhancer for purposes of gene expression or gene therapy and may have other utilities. Both factors can be used together to activate the CT/CGRP enhancer; however, the invention also includes use of the factors individually. The invention further includes other transcription factors which bind to the 18 bp DNA element and affect transcription under the control of the element.

The language "composition" is intended to include a mixture containing either or both factors described above. The composition includes preparations which contain the DNA binding activity, for example, cell extracts, partially purified or fully purified protein fractions, and cells expressing the gene of the cloned factors. The term further includes a composition of the proteins which also contains other factors or additives which do not block DNA binding or transcription activation.

The language "CT/CGRP enhancer" is intended to include a fragment of DNA which, when placed colinearly and in proximity to the CT/CGRP promoter will increase the rate of gene expression in neuroendocrine cells in the absence of agents from the superfamily of steroids and retinoids.

The language "binds to the site" is intended to include an activity which adheres to a sequence of DNA with an affinity such that random DNA oligonucleotides do not significantly compete the protein off of the binding site. In the present invention the binding sites were established by mutational analysis and electrophoretic mobility shift assays as described in the examples. The binding sites are claimed as CAGCTG and GTGCAAAT respectively. These binding sites are intended to include other sites which also bind the DNA binding proteins and mediate the regulation of CT/CGRP transcription.

The language "activity" is intended to include the act of binding to the site of the CT/CGRP enhancer. In particular, the activity is defined as the ability to form a complex in the electrophoretic mobility shift assay under the conditions described in the Materials and Methods.

The language "component of the HLH complex" is intended to include proteins which bind the CT/CGRP enhancer oligonucleotides under the conditions for the electrophoretic mobility shift assay described in the Materials and Methods section set forth below and migrate on the described polyacrylamide gel system at the same rate as the complexes identified as HB1 and HB2 in the FIG. 6.

The language "component of the OB2 complex" is intended to include proteins which binds the CT/CGRP enhancer oligonucleotides under the conditions for the electrophoretic mobility shift assay described in the Materials and Methods section set forth below and migrate on the described polyacrylamide gel system at the same rate as the complex identified as OB2 in the FIG. 6.

The language "represses transcription", "enhances transcription", and "recombinant expression vector" are intended as defined above.

The invention further encompasses a method for controlling gene expression using the above mentioned DNA binding factors. This method includes the insertion of a vector containing the CT/CGRP enhancer element and a gene the expression of which is to be controlled. Transcription of the gene is enhanced by the introduction of the proteins into the cell, whereby the proteins will bind to the enhancer element and activate transcription. The method includes introducing the proteins directly into the cell or expressing them from a recombinant vector containing DNA encoding the transcription factors. Moreover, the proteins can be expressed either from the same vector containing the gene of interest or a vector separate from the one containing the gene of interest.

The language "substantially purified proteins" is intended to include a composition of the above described proteins which is sufficiently pure to regulate CT/CGRP enhancer activity. Examples of compostions which can be used include nuclear extracts and fractions of such extracts obtained by methods well known in the art.

The language "purified DNA" is intended as defined above but in the context of the genes whose sequences code for the CT/CGRP enhancer binding proteins also described above. The purified DNA includes the sequence for the entire binding protein or a fragment of the protein. The purified DNA further includes the sequence either alone or in a DNA construct with other sequences, and it includes the sequence in a recombinant expression vector as defined above. Furthermore, the expression of the binding proteins from the purified DNA can be inducible, that is requiring the application of some agent for its activation, or it can be constitutive, that is requiring no agent or stimulus for its activation.

The language "gene of interest", "DNA construct", "expression vector" and "under conditions such that the expression of the gene of interest. is regulated" are all intended as defined above.

The invention is further illustrated by the following non-limiting examples. The contents of all of the references cited throughout this application, in particular Tverberg, L. A. and Russo, A. F. (1992) *Jour. Biol. Chem.* 267, 17567–17573 and Tverberg, L. A. and Russo, A. F. (1993) *Jour. Biol. Chem.* 268, 15695–15973, are expressly incorporated by reference.

EXAMPLES

Materials And Methods

Reporter Gene Constructs

Reporter fusion genes were constructed for experiments to localize cis-active elements responsible for glucocorticoid repression of the CT/CGRP gene. A series of 5' deletion constructs was made by restriction digestion of the plasmid pBSpAP (Stolarsky-Fredman, L., et al. (1990) *Mol. Endocrinol.* 4,497–504), a luciferase fusion gene containing the CT/CGRP gene 5' sequences fusing PstI (-1362), BglII (-920), DdeI (-717), and DraI (-163). These constructs are named -1900-CAL-LUC, -1362-CAL-LUC, -920-CAL-LUC,-717-CAL-LUC and -163-CAL-LUC respectively. Construction of the -1900 luciferase reporter plasmid (LphRI) and the -1125 luciferase reporter plasmid (Mu3) have been described by Stolarsky-Fredman, et al. All fragments share a common 3' terminus at position +21 in exon 1. To show that results were independent of the luciferase gene, the PstI (-1362) fragment was also inserted in front of the CAT reporter gene. An internal deletion of this -1363 CAT reporter gene was made by digestion and religation of the BglII sites at -1125 and -920 bp.

To construct the -920-1125 TK-LUC reporter gene, the -1125 to -920 BglII fragment was inserted into a BamHI site 5' to a TK-LUC reporter gene (Glass, C. K., Devary, O. V., and Rosenfeld, M. G. (1990) *Cell* 63, 729–738). The 920-1038- and 1039-1125-TK-LUC fusions contain blunt PvuII-BglII fragments subcloned into a blunt end TK-LUC BamHI site. The 1091-1017 insert was constructed using the polymerase chain reaction with flanking primers followed by ligation of BamHI linkers. The 1043-1025-TK-LUC insert was constructed by annealing complimentary oligonucleotides containing terminal BamHI sites.

To prepare constructs with mutant CT/CGRP enhancers, the mutant oligonucleotides were annealed and inserted upstream of the thymidine kinase promoter in TK-LUC.

Cell Lines, Culture Conditions and Transfection Assays

The 44-2C rat medullary thyroid carcinoma cell line was maintained in DMEM (high glucose) with 1% equine serum (HyClone Laboratories, Logan, Utah) and 0.1% L-glutamine; CA77 rat medullary thyroid carcinoma cells in Ham's F-12 medium/DMEM (low glucose)(1:1) with 10% fetal bovine serum (HyClone Laboratories); HeLa human epithelial derived cells in Ham's F-12 medium with 10% fetal bovine serum; and Rat1 fibroblast cells in DMEM (high glucose) with 10% calf serum. Also, 100 units/ml penicillin and 100 $\mu$g/ml streptomycin (GIBCO) were added to each culture medium.

Transfections were carried out by growing cells to approximately 80% confluency, harvesting them by brief trypsin/EDTA treatment, and resuspending them in $Ca^{2+}$/$Mg^{2+}$-free PBS. Approximately $10^7$ cells in 0.8 ml of PBS were electroporated with 20 $\mu$g of supercoiled DNA/cuvette (0.4-cm electrode gap, Bio-Rad) using a Bio-Rad gene pulser at 960 microfarads with the following voltages: 44-2C cells, 260 V; CA77, 220 V; HeLa, 250 V; and Rat1, 250 V. To ensure that DNA transfection conditions between control and dexamethasone-treated cells were equivalent, the cells were electroporated in a single cuvette and then split between two 6-cm dishes containing either serum-free medium supplemented with 5 $\mu$g/ml insulin, 5 $\mu$g/ml transferrin, and 5 ng/ml selenium (for CA77 cells only) or normal growth medium. Cells were immediately treated with 500 nM dexamethasone or the ethanol vehicle and then harvested 24 hours later.

In the retinoic acid experiments, the cells were treated essentially as above except that an apparently critical parameter for retinoic acid inhibition was that the CA77 cells could not be aggregated into clumps. To be consistent, all cell types were subcultured by trypsin treatment 1 day prior to the experiment, except for the 44-2C cells, which often required 2 days to firmly attach. About 4–5×10$^6$ cells in 0.8 ml were transfected with supercoiled DNA by electroporation using a Biorad Gene Pulser apparatus at 200 volts for the CA77 cells, 220 volts for the HeLa cells, and 260 volts for the 44-2C cells, all with a capacitance of 960 microfarads. The same amount of DNA (20 μg) was used per cuvette unless otherwise indicated. For the α-RXR cotransfection assays, 10 μg 18 bp CT/CGRP-TK-luc plasmid, 18 μg RSV-α-RAR plasmid, or 2 μg β-actin-RXR plasmid (brought to 30 μg total DNA with CMV-β-gal plasmid) were transfected into the cells (constructs described in Glass, C. K., S. M. Lipkin, O. V. Devary, and M. G. Rosenfeld (1989) Cell 59, 697–708; Glass, C. K., O. V. Devary, and M. G. Rosenfeld (1990) Cell 63, 729–738). The transfected cells from a single cuvette were then split between two 60 mm dishes and treated with 1 mM retinoic acid (Sigma) or the vehicle (0.01% ethanol). About 50 to 80% cell survival of the electroporation procedure was observed, except the 44-2C cells, in which approximately 25% of the cells were recovered. The cells were harvested 18–25 hours after transfection. Activities are reported per 50 μg protein unless otherwise noted.

Activity of the reporter genes and control constructs was measured by luciferase, CAT, or β-Galactosidase assays. To carry out the luciferase assays, cells were washed twice in PBS, harvested by scraping into PBS and then lysed in 100 μl of Triton lysis buffer (1% Triton X-100, 25 mM glycylclycine, pH 7.8, 15 mM MgSO$_4$, 1 mM dithiothreitol). After centrifugation, 20–50 μl of supernatant cell extract was assayed for luciferase activity as previously described (Braiser, A. R., Tate, J. E., and Habener, J. F. (1989) Biotechniques 7, 1116–1122) using a luminometer (Analytical Luminescence Laboratory Monolight 2001). The assay was linear between 100 (background) and at least 800,000 light units.

To assay for CAT activity, 5–40 μl of cell extract was heated to 65° C. for 10 minutes and then incubated with 300 μM n-butyryl coenzyme A and 100 μM chloramphenicol (Sigma) with 0.2 μCi of [$^3$H]chloramphenicol (DuPont-New England Nuclear, 30–60 Ci/mmol) in a volume of 100 μl of 250 mM Tris-HCl, pH 8.0. After 1–24 hours at 37° C., reaction products were isolated by extraction with 300 μl of xylene, back extracted twice, and counted in 5 ml of 4a20 scintillation fluid (Research Products International, Mount Prospect, Ill.) in a Beckman scintillation counter (described in Seed, B. and Sheen, J. Y. (1988) Gene (Amst.) 67, 273–277). The CAT assay was linear between 500 (background) and 50,000 cpm. Both luciferase and CAT assays were normalized to 50 μg of protein as determined by the Bradford protein assay (Bio-Rad) using bovine serum albumin as a standard. β-galactosidase assays were performed as described in Sambrook, J., Fritsch, E. F., and Maniatis, T. (1989) Molecular Cloning: A Laboratory Manual (Cold Spring Harbor Laboratory, Cold Spring Harbor, N.Y.) 2nd Ed.

Oligonucleotides and Electrophoretic Mobility Shift Assay

The following oligonucleotides were used in electrophoretic mobility shift competition assays:

| | | |
|---|---|---|
| H/O Enhancer | gatccGGCAGCTGTGCAAATCCTggatc | (SEQ ID NO:2) |
| HLH Mut | gatccGGACGCTGTGCAAATCCTggatc | (SEQ ID NO:3) |
| Oct Mut1 | gatccGGCAGCTGCGCAAATCCTggatc | (SEQ ID NO:4) |
| Oct Mut2 | gatccGGCAGCTGTGCAATGCCTggatc | (SEQ ID NO:5) |
| 5 bp Insert | gatccGGCAGCTGTGCTGTGCAAATCCTggatc | (SEQ ID NO:6) |
| 10 bp Insert | gatccGGCAGCTGTGCTAGAGTGTGCAAATCCTggatc | (SEQ ID NO:7) |
| AP-4(HLH) | AAGAACCAGCTGTGGAAT | (SEQ ID NO:8) |
| PAN(HLH) | GGCCAGAACACCTGCAGACG | (SEQ ID NO:9) |
| Octamer | GATCGAATCGAAATCACTAGCT | (SEQ ID NO:10) |
| Pit-1 | ccgaGCTTCATGAATATATATATAATCccga | (SEQ ID NO:11) |
| RARE | GGGTAGGGTTCACCGAAAGTTCACTCG | (SEQ ID NO:12) |

To perform electrophoretic mobility shift assays, nuclei were harvested from approximately 10$^8$ cells using a previously described miniextract preparation protocol, with one modification (Lee, K. A. W., and Green, M. R. (1990) Methods Enzymol. 181, 20–25). Instead of dialyzing the extract to remove excess NaCl, the extract was diluted 1:1 with extract buffer lacking NaCl. Aliquots of the diluted extract were stored at −70° C. Annealed oligonucleotide duplexes (10 pmol) containing recessed 3' termini were labeled for use as probes by incorporation of [$^{32}$P]dATP (25 μCi, 3000 Ci/mmol) using Klenow DNA polymerase. Both strands of blunt-ended oligonucleotides (10 pmol) were labeled separately using T4 polynucleotide kinase and [γ-$^{32}$P]ATP (20 μCi, 3000 Ci/mmol), then annealed. Unlabeled oligonucleotides used for competition assays were annealed and then treated with Klenow DNA polymerase if the ends were not already blunt. All probes and competitor DNAs were purified over Sephadex G50 columns.

The binding reaction (20 μl) contained approximately 3 μg (1–2 μl) of nuclear extract, 0.02 pmol of $^{32}$P-labeled DNA probe (50,000–100,000 cpm), 10 mM Tris-HCl, pH 7.5, 5% glycerol, 50 mM NaCl, 1 mM EDTA, and 1 mM dithiothreitol. Also, 0.1 μg of poly [d(I-C)] (Boehringer Mannheim) and 0.1 pmol of an unrelated double-stranded polylinker oligonucleotide (GATCCTCTA GACATATGG- GATC; SEQ ID NO: 13) were added as nonspecific competitors. Unlabeled competitors were preincubated with nuclear extracts 10 minutes on ice prior to addition of probe. After addition of probe, the reaction was incubated for 15 minutes on ice, then 2.5 µl of 50% glycerol dyes were added, and the samples were immediately loaded on a 6% polyacrylamide gel (1:29 bis:acrylamide) in 0.25× TBE (22.5 mM Tris-HCl pH 8.5, 28 mM boric acid, 0.7 mM EDTA). The gel was prerun for 1 hour prior to electrophoresis of the samples which was carried out for 3 hours at 200 V at 4° C. The gel was transferred to blotting paper, dried and exposed to X-ray film for 12–18 hours with an intensifying screen or for 3–4 days without a screen.

For the retinoic acid receptor element mobility shift experiments, the complementary RARE oligonucleotides (Glass, C. K., Devary, O. V., and Rosenfeld, M. G. (1990) Cell 63, 729–738) were labeled, annealed, and purified through a Sephadex G50 column. The binding reaction contained 3–6 µg nuclear extract from CA77 cells or 3 µg from HeLa cells. For some experiments, extracts were prepared from CA77 cells treated with 1 mM retinoic acid for 24 hours.

Purified bacterial GST fusion proteins containing nearly full-length human αRAR and human αRXR were obtained. The control GST fusion protein containing a fragment of a non-DNA binding protein were obtained. The integrity and concentrations of the fusion proteins were confirmed by Coomassie staining of SDS-polyacrylamide gels. The GST-RAR and GST-RXR fusion proteins were mixed in a 1:1 ratio at a concentration of 0.5–0.05 µg/µl (diluted as needed in binding buffer with 100 µg/µl BSA) and incubated on ice for 30 minutes to allow heterodimerization. For DNA binding assays, the receptor protein (0.5–0.05 µg for CA77 extracts and 0.05 µg for HeLa extracts) was added directly to a binding reaction containing the radiolabeled DNA probe as described above. For protein interaction studies, the receptor was preincubated in the binding reaction containing CA77 or HeLa nuclear extract for 15 minutes prior to addition of the probe. The reaction was then incubated for another 10 to 15 minutes and analyzed as described above.

Example 1
Identification of the 18 bp CT/CGRP Enhancer Element

Figure 1B:
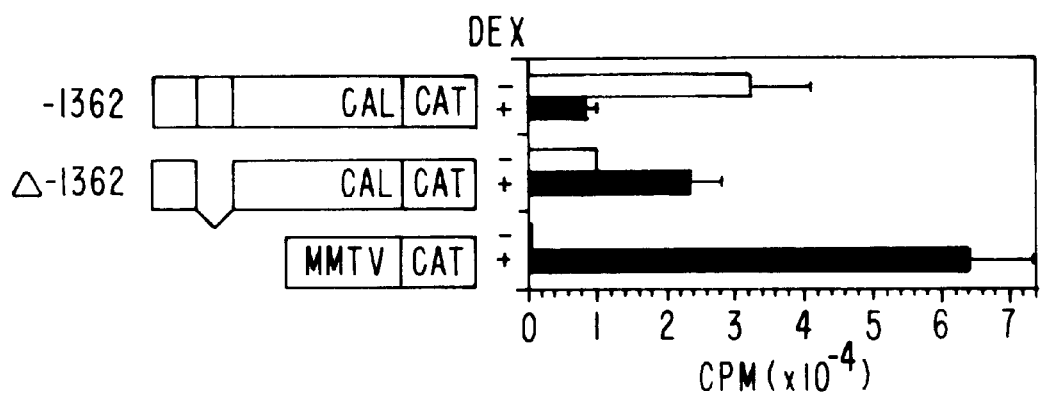

The mapping experiments were performed in 44-2C cells to show that sequences between 920 and 1125 bp from the transcription start site are responsible for negative regulation by dexamethasone (FIGS. 1A, B, C). FIG. 1A shows that dexamethasone repressed 2.5–4.5 fold the promoter activity of fusion genes containing at least 1125 bp of upstream sequences. In contrast, dexamethasone slightly stimulated gene activity from the shorter constructs. In addition to conferring dexamethasone-mediated repression, the -920-1125 region also enhanced basal transcription of the -1125-CAL-LUC fusion gene approximately 6-fold over that of shorter constructs. Repeating these experiments using bacterial CAT as a reporter gene demonstrated that these results were independent of the luciferase reporter gene (FIG. 1B).

Figure 1C:
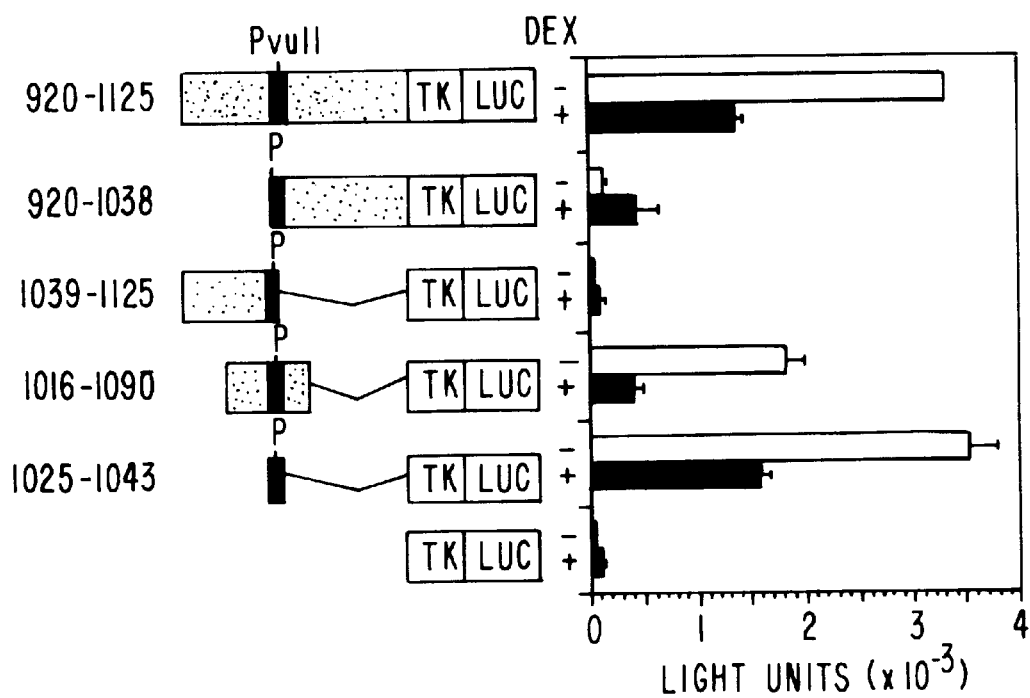

When the -920-1125 TK-LUC fusion gene was transfected into 44-2C cells, basal activity of the promoter was stimulated 70-90 fold over that of the thymidine kinase promoter alone (FIG. 1C). Treatment of the cells with 500 nM dexamethasone repressed the -920-1125 TI-LUC fusion gene expression 2.5–3 fold, although in a few experiments repression was as much as 10-fold. Thus, the cell-specific enhancement and repression were mediated by sequences within the -920-1125 element and could be transferred to a heterologous promoter. However, neither the -920-1038- nor the -1039-1125-TK-LUC fusions, which contain the fragments proximal and distal to the naturally occurring PvuII site in the CT/CGRP regulatory region, had much enhancer activity (less than 4-fold) and neither mediated repression by glucocorticoids. This result suggests that either the binding site was disrupted or that factors binding both upstream and downstream of the PvuII site are necessary for activity.

Smaller regions that span the PvuII site, the -1091-1017 and -1043-1025 elements, exhibited the same 24 fold repression as seen with the entire -920-1125 region and acted as strong enhancers of basal transcription (FIG. 1C). While the 74-bp fragment stimulated TK promoter transcription 40–50-fold, the 18-bp sequence between -1025 and -1043 bp was sufficient to enhance TK transcription 70–90-fold, to the same levels as the entire -920-1125-bp region. These results indicated that elements required for both full basal activity and repression by glucocorticoids are contained within a relatively small 18-bp region of the CT/CGRP promoter.

A luciferase gene containing the non-glucocorticoid-responsive thymidine kinase (TK) promoter was included as a control for nonspecific dexamethasone effects on reporter activity. As a positive control for dexamethasone responsiveness, the glucocorticoid-stimulated mouse mammary tumor virus (MMTV) promoter was coupled to CAT and transfected (FIG. 1B).

Figure 1D:
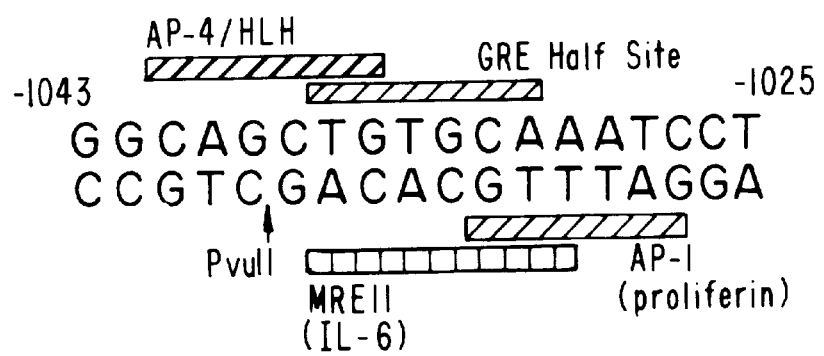
FIG. 1D shows the sequence of the identified 18 bp enhancer sequence (SEQ ID NO: 2) and potential binding sites. Sites found in the inverse orientation are indicated with a bar below the DNA sequence.

The sequence of the 18-bp element revealed a number of potential transcription factor binding sites based on sequence homologies (FIG. 1D). In particular, a site homologous to the right half of the palindromic GRE (TGTGCA) was found. In the inverse orientation, this sequence is contained within a previously described site of glucocorticoid repression in the interleukin-6 gene (TTGCACA) (Ray, A., LaForge, K. S., and Sehgal, P. B. (1 990) Mol. Cell. Biol. 10, 5738–5746). Also notable is a non-consensus AP-1 binding site (GATTTG) identified as part of an element mediating glucocorticoid repression of the proliferin gene (Diamond, M. I., et al. (1990) Science 249, 1266–1272; Mordacq, J. C. and Linzer, D. I. H. (1989) Genes & Dev. 3, 760–769). The 18-bp element also contains a possible site for HLH transcription factor binding (CAGC TG) identical to the AP-4 HLH factor site found in the SV40 promoter (Mermod, N., Williams, T. J. and Tjian, R. (1988) Nature 132, 557–561, Hu, Y., r al (1990) Genes & Dev. 4, 1741–1752). The importance of this site is underlined by the fact that when the site is disrupted, almost all transcription enhancement is abolished.

Example 2
Dose-dependence of dexamethasone-mediated repression

Figure 2:
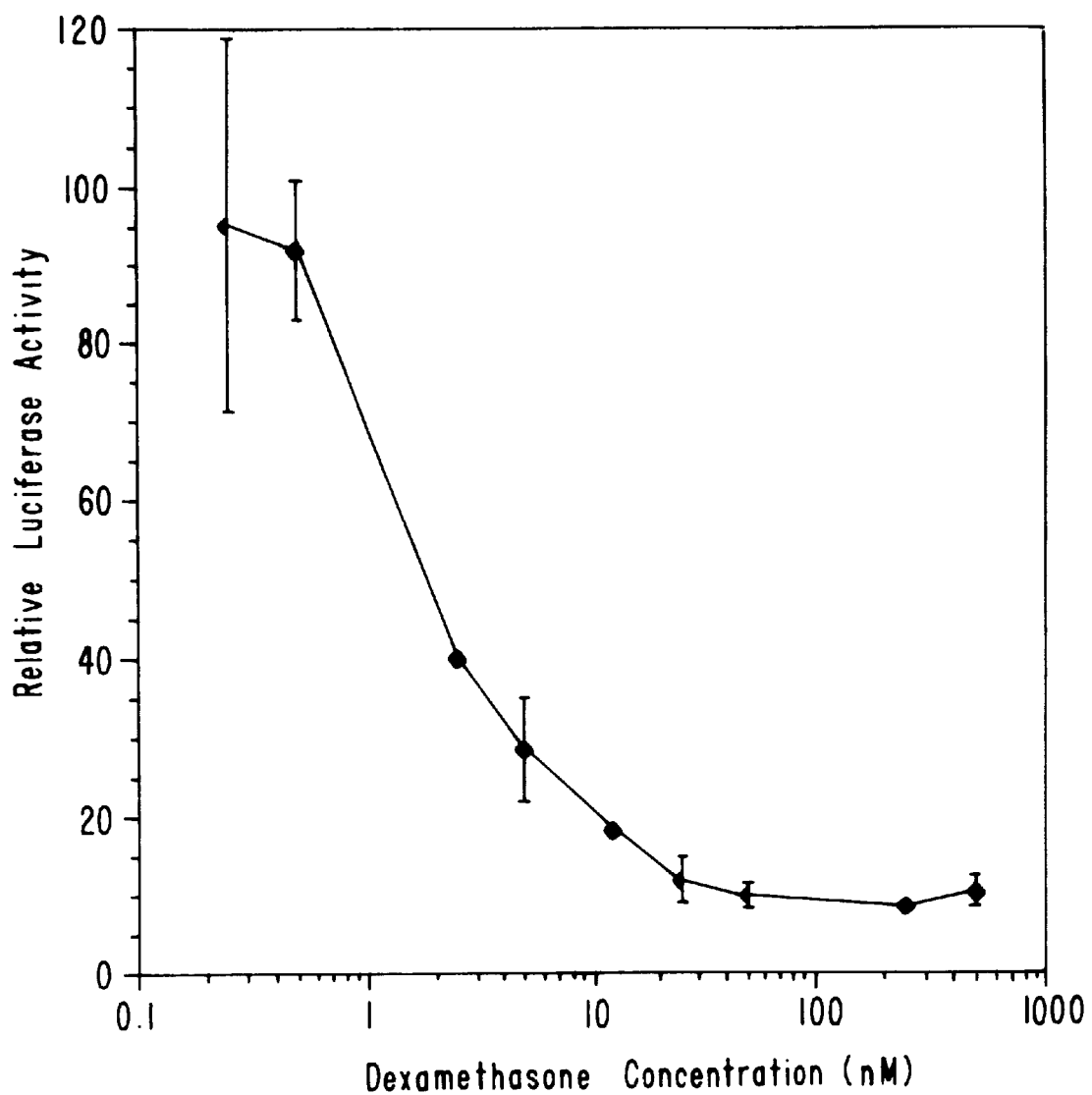
FIG. 2 is the dose response curve for dexamethasone repression of -920-1125-TK-LUC activity in 44-2C cells. Cells were incubated with various concentrations of dexarnethasone or the equivalent dose of the ethanol vehicle for 24 hours, and then cell extracts were assayed for luciferase activity/ag protein. Activity was normalized to that of each vehicle-treated cell extract, approximately 80,000 light units/50 µg of protein. The means and standard deviations of two experiments are shown.

The dexamethasone dose dependence of promoter repression was determined to characterize the type of receptor involved. 44-2C cells were transfected with the -920-1125-TK-LUC plasmid and incubated with dexamethasone concentrations between $10^{-11}$ and $10^{-6}$ M for 24 h. An equivalent amount of the ethanol vehicle was added to each control plate. Promoter activity was repressed approximately 10-fold at dexamethasone concentrations above 50 nM (FIG. 2). Inhibition was half-maximal with a dexamethasone concentration of 2.5 nM, which is a very close to the previously reported dexamethasone $K_d$ range 3–10 nM for the involvement of the glucocorticoid receptor in repression of calcitonin/CGRP transcription (Pressely, L. and Funder, J. W. (1975) Endocrinology 97, 588–596; Manz, B., Grill, H. J., Kreienberg, R., Rehder, M., and Pollow, K. (1983) J. Clin. Chem. Clin. Biochem. 21, 69–75).

Example 3
Cell Specificity of the Dexamethasone Mediated Repression

The effect of the -920-1125 enhancer region on transcription was next investigated in the CA77 thyroid C cell line, where the endogenous calcitonin/CGRP gene is stimulated by glucocorticoids. Reporter genes containing up to 1900 bp of the calcitonin/CGRP promoter sequence were assayed in this cell line. As with 44-2C cells, the -920-1125 region in CA77 cells stimulates basal transcription of the calcitonin/CGRP promoter 8-12-fold (FIG. 3A). However, in the CA77 cell line, dexamethasone treatment did not repress activity of calcitonin/CGRP promoter fusion genes containing the -920-1125-bp element. This result indicates that, as with the endogenous gene, glucocorticoids differentially regulate reporter gene activity in these two cell lines.

Overexpression of glucocorticoid receptor in CA77 cells did not cause repression of either -1900-CAL-LUC or -920-1125-TK-LUC reporter activity; thus, the lack of repression in the CA77 cell line was not caused by lower glucocorticoid receptor levels. Furthermore, as a control to show that glucocorticoids are able to stimulate reporter gene expression in both CA77 and 44-2C cell lines, a CAT fusion gene containing the glucocorticoid-responsive MMTV promoter was transfected into both cell types (FIGS. 1A and 3A). In both CA77 and 44-2C cell lines, CAT activity was stimulated to similar levels with greater than 100-fold increases. CA77 and 44-2C cells thus appear capable of similar transactivation by glucocorticoids.

In the CA77 cells, as in 44-2C cells, the entire -920-1125 region strongly enhanced TK promoter transcription, stimulating activity 30–40-fold. Sequences proximal to the PvuII site at -1038 bp had only 7% of full enhancer activity while distal sequences had no effect on TK-LUC transcription (FIG. 3B). This result indicated that the intact PvuII site is also necessary in CA77 cells for enhancer function. The 74- and 18-bp elements conferred only 9 and 27%, respectively, of the full activity of the -920-1125 region. This is in contrast to the 44-2C cells in which the 18-bp element alone enhanced transcription equally as well as the entire -920-1125 region. Presumably, other transcription factors that bind outside these regions contribute to full enhancer activity in the CA77 cell line. Dexamethasone repressed activity of the -920-1125-bp region by a small but statistically significant amount (1.2-fold, p<0.05). The repression was more pronounced (1.6-fold, p<0.01) with smaller elements that include the 18-bp region.

Figure 3C:
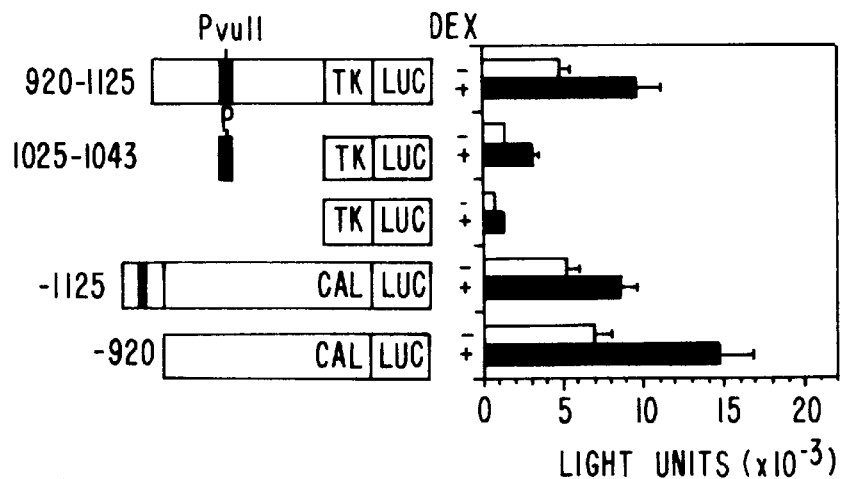
Figure 3D:
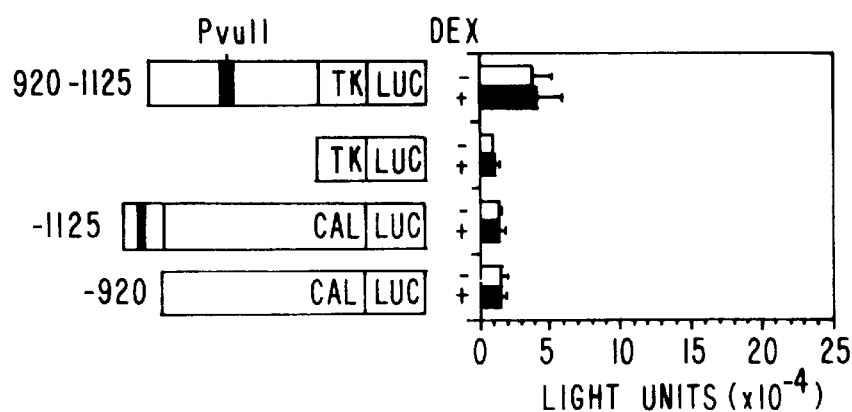

The dependence of dexamethasone regulation on cell-specific factors was further tested by transfection of the fusion gene constructs into non-neuroendocrine cells. In both the HeLa and Rat1 fibroblast cells, as shown in FIGS. 3C and D, the neuroendocrine-specific -920-1125 enhancer did not increase calcitonin promoter activity and dexamethasone did not repress activity of the enhancer in this cell line. In the two cell lines, the calcitonin-luciferase fusion genes without the -920-1125 region were equally as active as those with the region. When the -920-1125 region was placed upstream of the TK-LUC gene, it increased transcription approximately 7-fold in the HeLa cell line and 3-4-fold in the Rat1 cell line as compared to the 40-80 fold enhancement seen in CA77 or 44-2C cells. In HeLa cells, the 18-bp element alone stimulated TK promoter activity only 2-fold. Dexamethasone treatment did not repress activity of either CT/CGRP or TK promoter fusion genes but uniformly stimulated reporter activity of all plasmids 1.5–2-fold, including the TK-LUC reporter gene, which does not contain a glucocorticoid-response element.

Figure 3E:
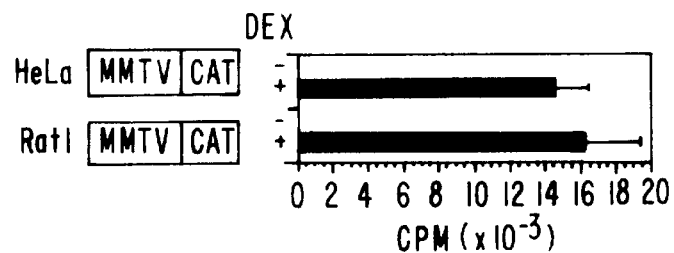
FIG. 3E shows dexamethasone response of glucocorticoid receptors expressed in MMTV-CAT transfected Hela and Rat 1 cells.

To establish that both cell lines expressed glucocorticoid receptors and were capable of responding to dexamethasone, the MMTV-CAT gene was transfected into the cells. In the absence of dexamethasone, promoter activity was below the limits of detection, but upon dexamethasone treatment, activity was stimulated at least 100-fold in both Rat1 and HeLa cells (FIG. 3E). Thus, dexamethasone does not fail to repress genes containing the -920-1125 enhancer element because of a lack of functional glucocorticoid receptors. Multiple DNA preparations and co-transfection controls were included to show that results were not DNA-or transfection- dependent.

Example 4
Mutation Analysis of the CT/CGRP Enhancer Element

Figure 4A:
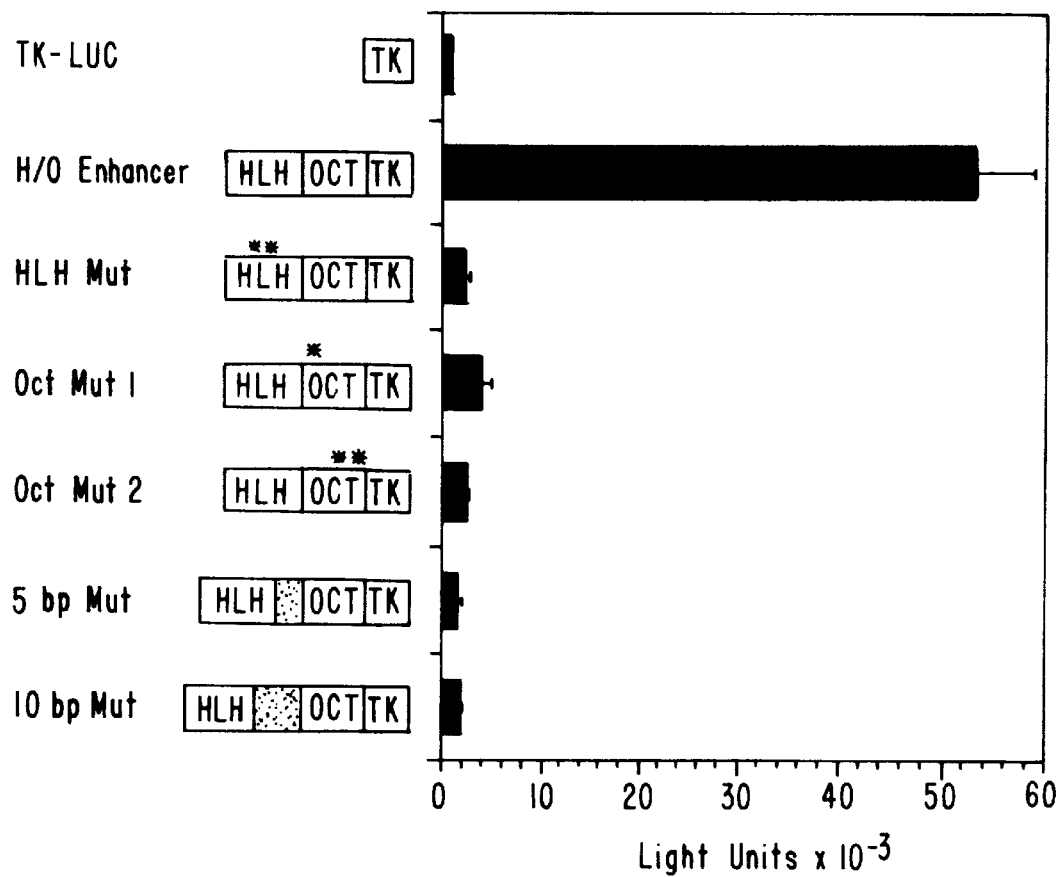
FIGS. 4A and 4B shows the luciferase activity from the wild type and mutant CT/CGRP enhancers in 44-2C (FIG. 4A) and HeLa (FIG. 4B) cell lines. Cells were transfected and incubated 18 to 24 hours, then assayed for luciferase activity. The activities are shown as means and standard deviations from three to eight independent experiments normalized to the average activity of TK-LUC. The activities are reported per 50 µg of extract. Mutations are indicated as asterisks.
Figure 4B:
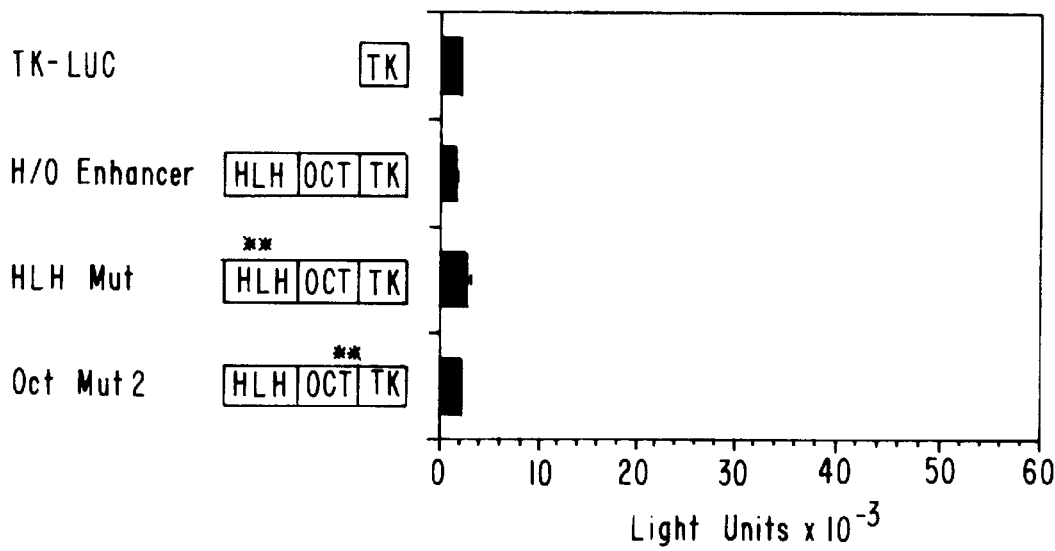

While the presence of wild type enhancer element stimulated luciferase gene activity approximately 50-fold from the TK promoter in TK-LUC, mutations in either the HLH or octamer sites essentially abolished enhancer activity. FIG. 4 presents data demonstrating that the mutant HLH and octamer enhancers stimulated activity less than 3- and 5-fold, respectively. These results demonstrate two points. First, the mutations establish the functional significance of the HLH and octamer motifs. Second the 50-fold enhancement elicited by the wild type element containing both the HLH and octamer motifs is greater than predicted from the activity of the mutant enhancers containing only one of the motifs. Consequently, the requirement for both HLH and octamer sites suggests that factors that bind these sites activate transcription in a synergistic manner.

Furthermore, the separation of the HLH and octamer motifs was assayed for its effect on enhancer activity. The sites were separated by inserting 5 or 10 bp, corresponding to about a half or full helical turn, respectively. Transfection analyses showed that both the 5- and 10-bp insertions greatly reduced enhancer activity, having less than a 2-fold stimulatory affect on TK-LUC activity (FIG. 4A). These data indicate that the HLH and octamer motifs must be in close proximity to activate transcription. However, although the motifs were preserved, the insertions may still have affected binding of the HLH and/or octamer factors.

To determine whether the HLH or octamer motifs of the CT/CGRP enhancer might act independently in non-C-cell lines, the wild type and mutant enhancer reporter genes were transfected into HeLa cells. In the case of the CT/CGRP enhancer, FIG. 3B shows that both the wild type and mutant forms had similar activities in HeLa cells.

Example 5
Enhancement of Transcription in HeLa Cells by Co-transfection of the MASH1 Gene.

The CT/CGRP enhancer was tested for activation by an HLH factor as predicted by the mutation studies. The approach was to co-transfect the mammalian achaete-scute homologue-1 (MASH1) HLH transcription factor (Johnson, J. E., Birren, S. J., and Anderson, D. J. (1990) *Nature* 346, 858–861). along with the CT/CGRP enhancer. The luciferase fusion construct was transfected along with an expression plasmid containing the MASH1 gene linked to a cytomegalovirus (CMV) promoter. Control plates were co-transfected with the CMV-B-galactosidase fusion gene to maintain a constant amount of DNA in the transfections and to control for possible nonspecific effects of the strong CMV promoter. The CMV-β-galactosidase vector did not have any detectable effect on TK-LUC reporter gene activity.

Figure 5:
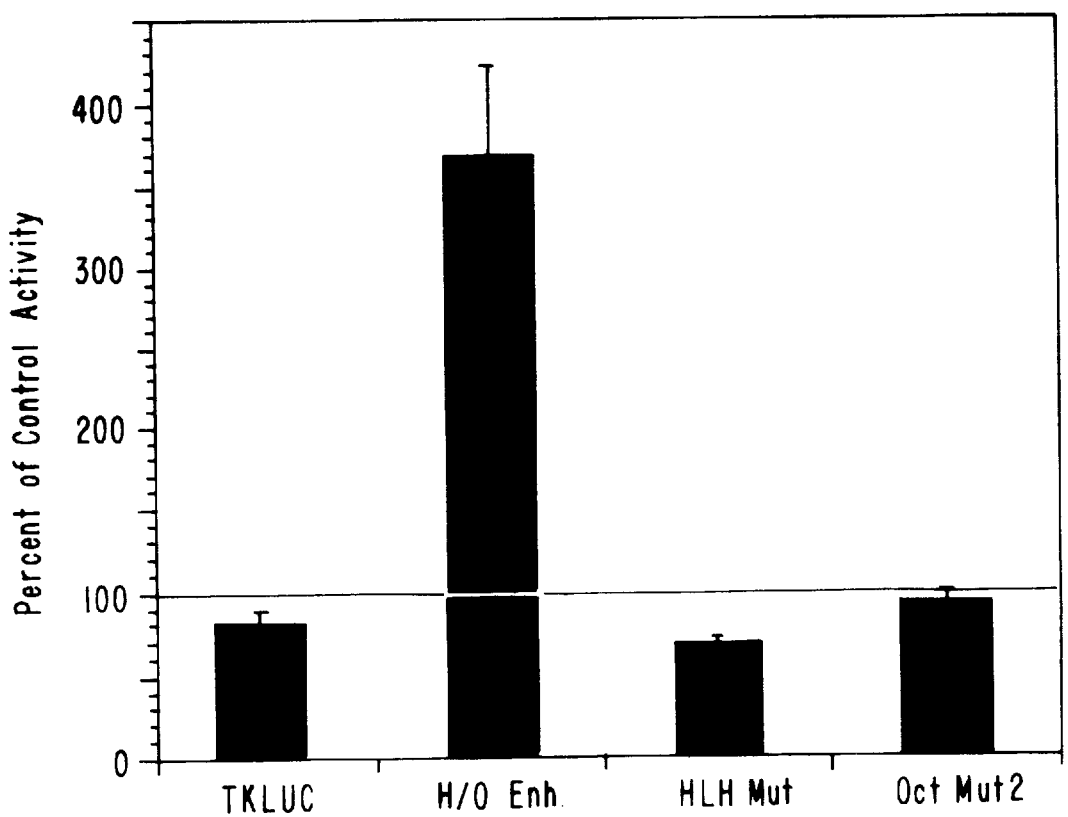
FIG. 5 presents data from experiments testing the induction of CT/CGRP enhancer activity by co-transfection of a MASH expression vector. HeLa cells were co-transfected with the enhancer-TK-LUC reporter gene and either the CMV-MASH1 plasmid or CMV-β-galactosidase plasmid as a control. The luciferase activity for each of the reporter genes in control cells was set at 100%. The activity of the CMV-MASH1 transfected cells is shown relative to the control cells as the means and standard deviations from three experiments.

Co-transfection of the MASH1 expression vector activated the CT/CGRP enhancer element approximately 4-fold in HeLa cells (FIG. 5). As a control for specificity of MASH1 action, co-expression of MASH1 had little or no effect on the TK-LUC reporter gene lacking the CT/CGRP enhancer. Likewise, MASH1 stimulation was not observed with the reporter genes containing mutant forms of the CT/CGRP enhancer. A somewhat unexpected observation was that MASH1 did not activate the enhancer even when the mutation was in the octamer binding site and the HLH site was unaffected. The lack of enhancement of the octamer site mutants supports the prediction that enhancement requires both the HLH and octamer motifs.

Co-transfection of the MASH1 expression vector in CA77 cells yielded a smaller degree of stimulation (2-fold), and no significant effect could be detected in the 44-2C cells (data not shown). One explanation for the diminished effect of co-transfected MASH1 in the C cell lines is that the HLH binding factor is not limiting in these cells. In either case, the transactivation results demonstrate that the CT/CGRP enhancer can be transactivated by HLH transcription factors.

Example 6
Analysis of Protein Complex Formation on the CT/CGRP Enhancer

Figure 6A:
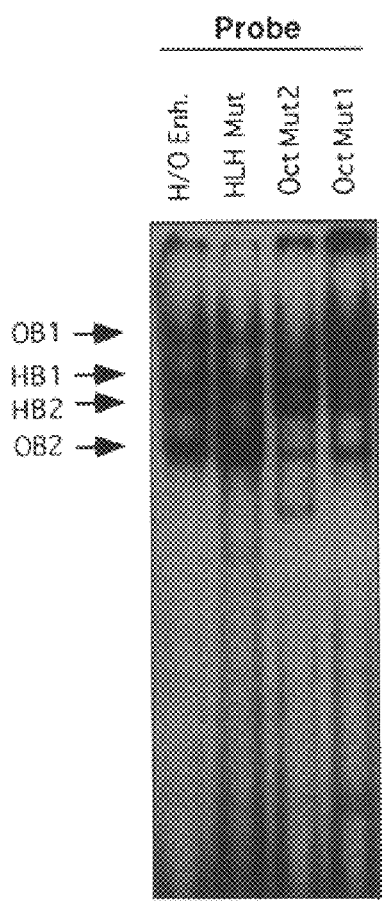
FIGS. 6A, 6B, and 6C show mobility shift analysis of complexes binding the CT/CGRP enhancer.

Several complexes were observed with nuclear extracts prepared from the 44-2C cells using a radiolabeled oligonucleotide containing the 1 8-bp CT/CGRP enhancer as a probe. The wild type enhancer probe bound five complexes, designated as HL1, HL2, OB1, OB2, and H/OB for CT/CGRP enhancer HLH (HL) or octamer-binding (OB) factors (FIG. 6A).

The significance and identity of these five complexes were elucidated using the functionally inactive point mutants as mdiolabeled probes and as unlabeled competitors in the binding assay. The CT/CGRP enhancer oligonucleotide probe containing a mutation in the HLH motif gave a different DNA-protein complex profile than seen with the wild type enhancer. The HLH mutant oligonucleotide did not form either the HB1 or HB2 complexes but did form both the OB1 and OB2 complexes (FIG. 6A). The binding of the octamer proteins in the absence of HLH binding indicates that these two classes of factors can bind the enhancer individually, at least in vitro. These results demonstrate that the HLH motif is required for HB1 and HB2 but not for OB1 and OB2 complex formation.

Two different CT/CGRP enhancer oligonucleotides with mutations in the octamer motif (Oct Mut1 and Oct Mut2) reduced the formation of OB2 complex, although factor binding was not completely abolished. As with OB2, OB1 complex formation was also greatly reduced on the Oct Mut2 oligonucleotide probe. However, the Oct Mut1 probe bound OB1 more strongly than did the wild type enhancer (FIG. 6A). Because the Oct Mut1 element exhibited 10-fold decreased enhancer activity this result indicates that binding of OB2 to the 18-mer is likely to be necessary for enhancer activity. Both octamer mutants bound the HB1 and HB2 complexes, demonstrating that the reduced octamer binding activity did not significantly affect HLH binding. Thus, according to these results, the OB1 and OB2 complexes interact with the octamer half of the CT/CGRP enhancer and that the binding specificity of these two factors may differ.

Figure 6B:
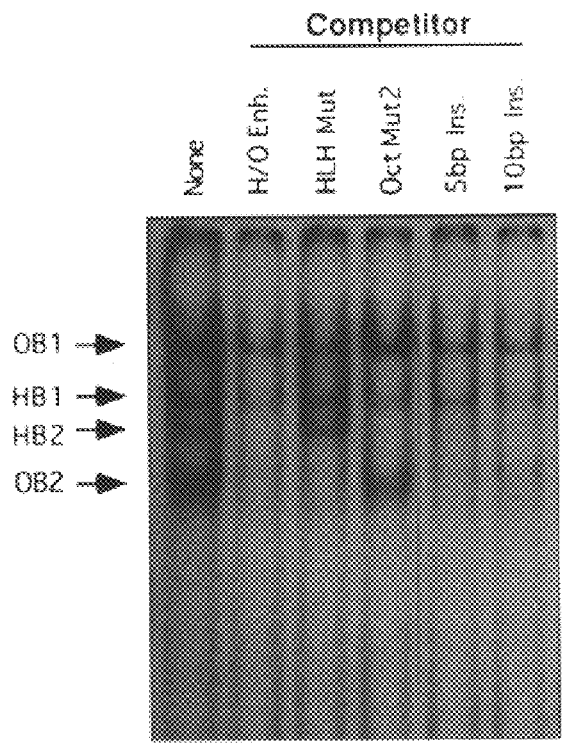

The specificity and identity of the complexes seen on the CT/CGRP enhancer were confirmed with competition binding assays using excess wild type and mutant unlabeled CT/CGRP enhancer oligonucleotides. Competition with the wild type CT/CGRP enhancer diminished the formation of the HB1, HB2, OB1, and OB2 complexes. Competition with the oligonucleotide containing the CT/CGRP enhancer HLH mutation did not remove HB1 and HB2, yet did reduce binding of OB1 and OB2 (FIG. 6B). This result is consistent with the above conclusion that the HB1 and HB2 complexes bind to the HLH motif. Conversely, oligonucleotides containing mutations in the CT/CGRP enhancer octamer motif did not remove the OB1 and OB2. complexes to the same extent as the wild type or HLH mutant oligonucleotides (FIG. 6B). The partial competition for OB1 and OB2 complexes is expected since these mutations did not completely abolish binding, as shown previously. As expected, the octamer mutant oligonucleotides did reduce the HB1 and HB2 complexes. These results confirm that the OB1 and OB2 complexes form on the octamer motif.

Example 7
Competition Assays with Known Transcription Factor Binding Sites

Figure 6C:
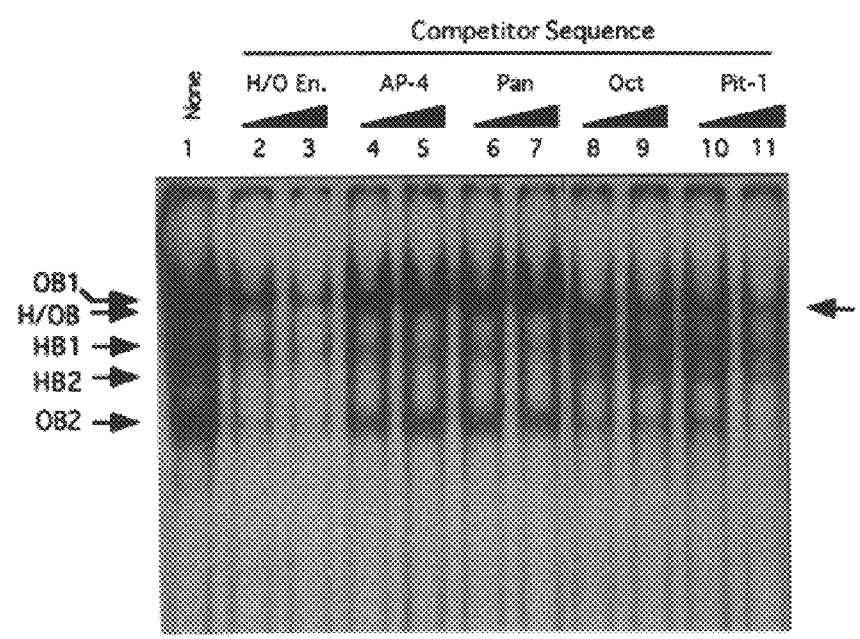

The complexes identified by their affinity for motifs on the CT/CGRP enhancer were tested for their ability to bind known octamer and HLH transcription factor binding sites. Binding was assayed by competition with oligonucleotides encoding these known sites which are flanked by sequences unrelated to the CT/CGRP enhancer. Oligonucleotides containing either the AP-4 HLH binding site (Mermod, N., Williams, T. J., and Tjian, R. (1988) *Nature* 332, 557–561) or the Pan HLH binding site (Nelson, C., et al. (1990) *Genes & Dev.* 4, 1035–1043) reduced HB1 and HB2 complex formation. The OB1 and OB2 complexes were relatively unaffected by these oligonucleotides (FIG. 6C). Conversely, competition with either the consensus octamer binding site (Scholer, H. R. (1991) *Trends Genet.* 7, 323–329) or the related Pit-1 POU protein binding site (Nelson, C., et al (1988) *Science* 239, 1400–1405) selectively removed the OB1 complex. Removal of OB2 and the H/OB complex required higher concentrations of these competitors (FIG. 6C). These experiments indicate that the complexes that form on the CT/CGRP element are most likely HLH and octamer-binding proteins.

The HLH and octamer-containing H/OB complex was detectable when complexes were resolved after competition of the OB1 complex or when the mobility shift assays were electrophoresed for longer times. Competition with the wild type enhancer or the enhancer containing a mutation in either the HLH or octamer binding sites specifically removed the H/OB complex. This result suggests that the H/OB complex may contain factors that bind to both HLH and octamer motifs. Low amounts of Pit-1 or octamer competitor oligonucleotides preferentially removed OB1 relative to OB2, suggesting that the H/OB complex contains OB2. Furthermore, the relative migration rates of the complexes suggest that the H/OB complex contains OB2 and HB1 or HB2.

Mobility shift competition assays showed that OB1 and OB2 complexes have different affinities for the consensus octamer and the CT/CGRP enhancer. As mentioned above, higher concentrations of Pit-1 and octamer consensus competitors were required to remove OB2 than OB1 binding. As little as 5-fold excess unlabeled enhancer substantially reduced OB2 binding but had little effect on OB1 binding to the CT/CGRP enhancer. In contrast, 5-fold excess of the consensus octamer oligonucleotide removed most of OB1 binding but did not affect OB2 binding to the element. Moreover, it was difficult to fully compete the OB1 protein from the CT/CORP enhancer using the H/O enhancer as competitor possibly because there is a large excess of OB1 protein in the extracts and OB1 has a relatively weak affinity for the H/O enhancer. In agreement with this observation, much more OB1 protein bound to the consensus site compared with the CT/CGRP enhancer and competition with 10-fold excess octamer DNA removed OB1 binding from the octamer more effectively than 250-fold excess CT/CORP enhancer DNA. This result demonstrates that OB1 has at least 25-fold higher affinity for the octamer consensus relative to the CT/CGRP enhancer octamer site. A lower band that co-migrated with the OB2 complex binds very weakly to the octamer site and is removed by 10-fold excess of either oligonucleotide. Thus, results indicate that OB1 protein has higher affinity for the octamer consensus relative to the CT/CGRP H/O enhancer, whereas the OB2 protein has higher affinity for the CT/CGRP H/O enhancer.

Example 8

Effect of Oct Antiserum on Binding of OB1 and OB2 to the CT/CGRP Enhancer

To further characterize the OB1 and OB2 complexes, a polyclonal antiserum raised against the POU domain of the human Oct-2 protein was tested for its ability to block complex formation. This antiserum has been shown to block Oct-1 binding to DNA in a mobility shift assays (Kristie, T. M., LeBowitz, J. H., and Sharp, P.A. (1989) *EMBO J.* 8, 4229–4238). Preincubation with the Oct antiserum prevented OB1 but not OB2 from binding to the CT/CGRP enhancer and to the consensus octamer site. The inability of the antiserum to block OB2 complex formation suggests that the OB2 protein is significantly different than the Oct-1 and Oct-2 octamer-binding proteins. A complex corresponding to H/OB was observed following preincubation with the antiserum. This result is consistent with the increased detection of H/OB following reduction of the OB1 complex by competition with Pit-1 or consensus octamer oligonucleotides. Furthermore, the comigrating OB1 complex had the same property in both 44-2C and CA77 cell extracts. As seen with 44-2C extracts, the Oct antiserum blocked OB1 formation with both the CT/CGRP enhancer and the octamer consensus probes with HeLa extracts. The observations that OB1 was present in HeLa extracts (and all other extracts tested), was relatively large by mobility shift assays, and was recognized by the Oct antiserum strongly suggest that OB1 is the Oct-1 protein. Oct-1 is known to be a ubiquitously expressed transcription factor that is larger than any other known octamer factor (Scholer, H. R. (1991) *Trends Genet* 7, 323–329).

Example 9

Cell Specificity of Complex Formation on the CT/CORP Enhancer

To identify whether any of the CT/CGRP enhancer complexes were cell-specific, extracts from the CA77, HeLa and Rat1 cell lines were compared in mobility shift experiments containing the radiolabeled CT/CGRP enhancer oligonucleotide. The HLH and octamer binding complexes were identified by competition with 25-fold excess unlabeled AP-4 HLH or octamer consensus oligonucleotides. Based on these criteria, extracts from all three cell lines formed complexes that co-migrated with OB1 and HB2. The cell lines containing enhancer activity (44-2C and CA77) also contained the OB2 and HB1 complexes. Neither HeLa nor Rat1 nuclear extracts promoted formation of the OB2 or HB1 complexes (FIGS. 7A and B).

Figure 7A:
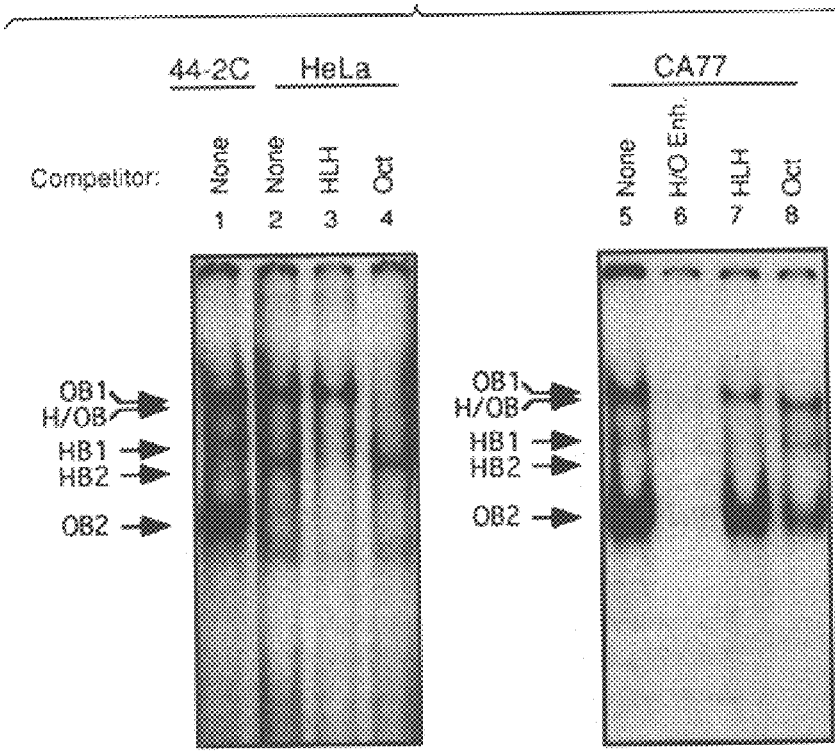
FIGS. 7A, 7B, and 7C show a comparison of the CT/CGRP enhancer-binding complexes in CA77 and HeLa cell extracts.
Figure 7B:
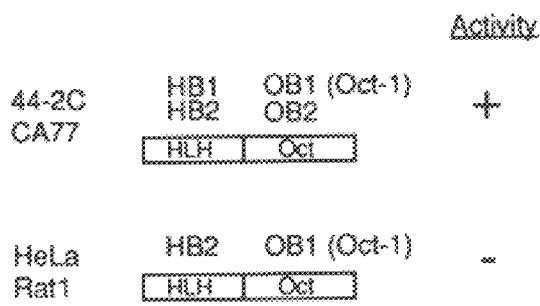
Figure 7C:
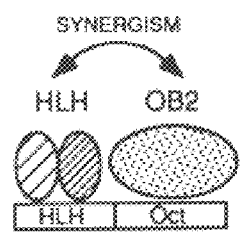

CA77 extracts had low levels of HB2 which were more visible with longer exposure times or competition with the Oct Mut2 probe (FIG. 7A). In addition, the complexes observed with CA77 extracts bound the mutant enhancer probes in a manner similar to that seen with 44-2C extracts. In particular, OB2 bound the HLH mutant probe to a greater extent than it bound the wild type probe and more tightly than OB1 bound the Oct Mut1 probe. The H/OB complex was often more readily detected in CA77 extracts than in 44-2C extracts as a complex migrating slightly faster than OB1. As seen with the 44-2C extracts, H/OB was clearly detected in CA77 cell extracts when the OB1 complex was removed by octamer competition. The H/OB complex was not seen with HeLa or Rat1 extracts. Based on the cell specificity and mutation studies, a model for the mechanism of CT/CGRP enhancer activity is schematically shown in FIG. 7C.

Example 10

Retinoic Acid Repression Mediated by the CT/CGRP Enhancer Element

Retinoic acid treatment of CA77 cells had been shown to cause about a 2–3-fold decrease in calcitonin and CGRP mRNA levels (Russo, A. F., T. M. Lanigan, B. E. Sullivan. (1992) *Mol. Endocrinol.* 6,207–218). To determine if the reduction of mRNA levels could be due to a decrease in transcription, the effect of retinoic acid on promoter activity was determined.

Figure 8A:
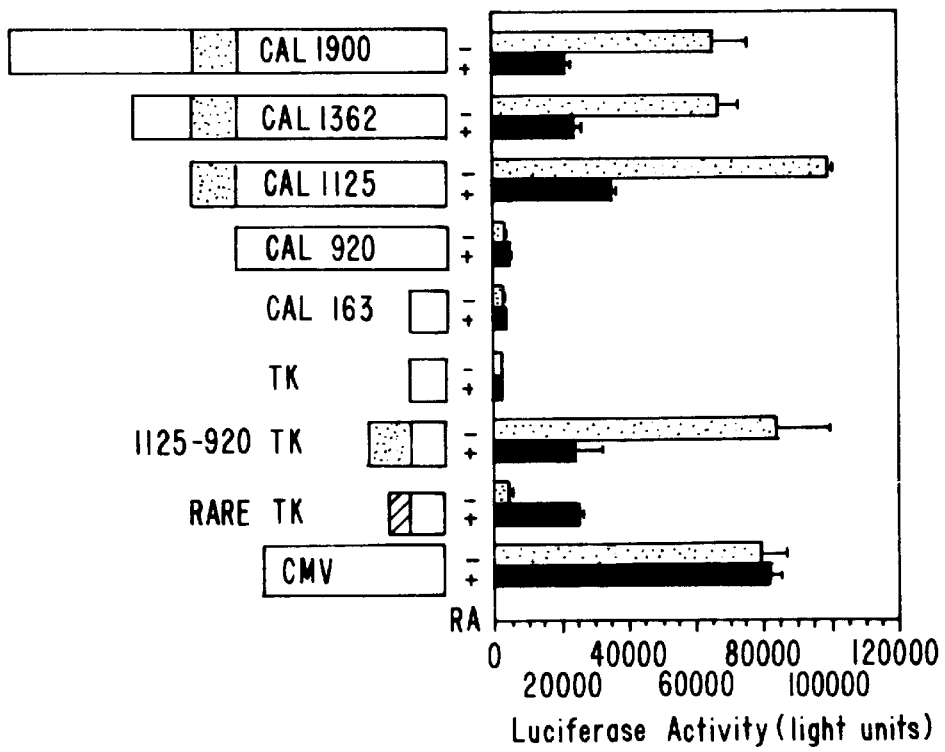
FIGS. 8A and 8B show the effect of retinoic acid on expression from the CT/CGRP promoter and enhancer deletion constructs.

Retinoic acid treatment caused a 2–3-fold decrease in the promoter activity of luciferase fusion genes containing 1125 bp or more 5' flanking sequences (FIG. 8a). In contrast, promoter fragments containing 920 bp or less were not repressed by retinoic acid. This result suggested that the retinoic acid responsive element lies between 920 and 1125 bp 5' of the transcription initiation site. Furthermore, the basal activity of fusion genes containing the -920-1125 region was about 10–20-fold greater than constructs containing this region (FIG. 8A). It should be noted that despite the lower activity, the plasmids lacking enhancer activity still express sufficient luciferase activity (usually 5000 light units above the background of about 100 light units) such that repression, if it occurred, could have been detected.

As a control to confirm that CA77 cells contained functional retinoic acid receptors that could stimulate transcription and to confirm the specificity of repression, the cells were transfected with a luciferase reporter gene containing two tandem repeats of the retinoic acid responsive element from the β-retinoic acid receptor gene linked to the thymidine kinase promoter (RARE-TK-luc, Glass, C. K., O. V. Devary, and M. G. Rosenfeld. (1990) *Cell* 63, 729–738). A consistent 5-fold increase in RARE-TK-luc activity was observed upon retinoic acid treatment (FIG. 8A). As additional controls for the specificity of the retinoic acid effects, cells were transfected with luciferase fusion genes containing the cytomegalovirus promoter (CMV-luc) or the thymidine kinase promoter (TK-luc), which were not significantly affected by retinoic acid (FIG. 8A).

The next objective was to document that the sequences required for repression were localized within the region defined by the deletion studies. The deletion construct 1 125-920-TK-luc was transfected into the CA77 cells. As expected, the basal activity of TK-luc was enhanced about 30-fold by the 1125-920 bp region, confirming the presence of enhancer activity. Treatment of the cells with retinoic acid caused a 34-fold repression in 1125-920-TK-luc activity (FIG. 8A). Repression was seen with the fragment in both orientations (data not shown). In transfection experiments using the TK promoter-luciferase gene fusion constructs in CA77 cells, treatment of the cells with retinoic acid caused a 3–4-fold repression in the 1125-920-TK-luc activity. Repression was seen with the fragment in both orientations. These results demonstrate that the retinoic acid responsive element is contained entirely within the cell-specific enhancer region, and furthermore, that retinoic acid repression is transferable to a heterologous promoter.

Figure 8B:
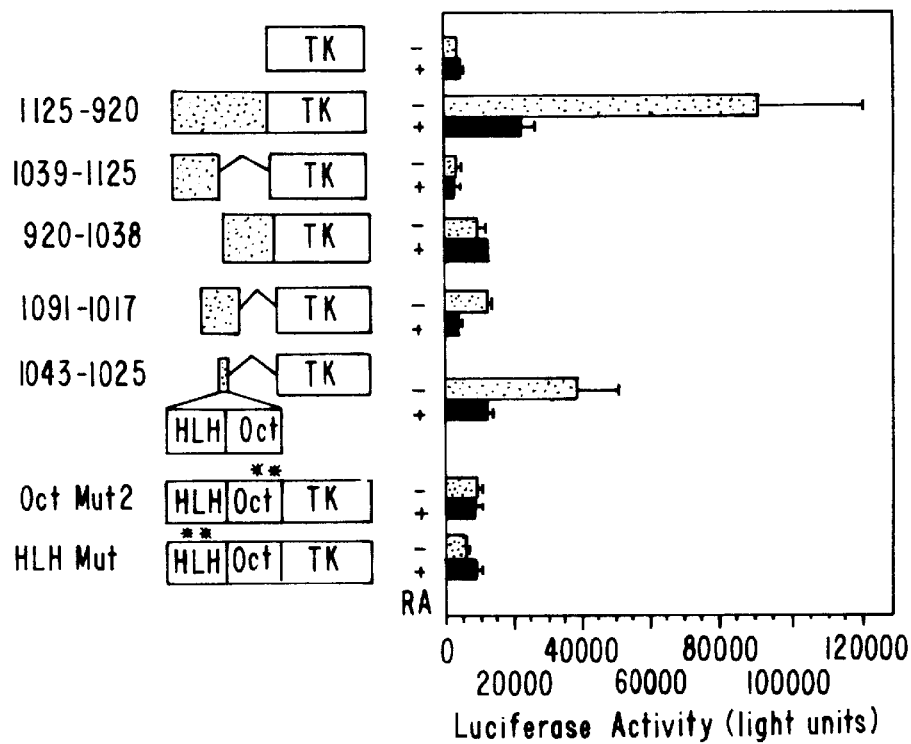

The sequences required for repression were further mapped within the 1125-920 bp region using the TK promoter-luciferase gene fusion constructs. Neither 1039-1125-TK-luc nor 920-1038-TK-luc exhibited retinoic acid dependent repression or retinoic acid independent enhancement of basal transcription (FIG. 8B). Similar results were seen with the CT/CGRP upstream fragments in the opposite orientation. The TK-luc vector, 1091-1017-TK-luc, having the 75 bp fragment spanning the PvuII site, had relatively little enhancer activity (only 3–4-fold) while 1043-1025-TK-luc, containing the 18 bp fragment, was more active, with 8–12 fold enhancement over TK-luc (FIG. 8B). For comparison, in parallel experiments the full 205 bp element yielded about 20-fold enhancement. Thus, reporter genes whose expression was controlled by the 75 bp and 18 bp fragments exhibited retinoic acid dependent repression that was comparable to the full 205 bp region. Consequently, both retinoic acid repression and most enhancer activity was localized to the 18 bp element.

Furthermore, neither the HLH or Oct mutant constructs conferred retinoic acid repression or had very much enhancer activity (2-fold or less; FIG. 8B). The loss of retinoic acid dependent repression with the point mutations indicates that both the HLH and octamer motifs are required for repression.

Control experiments demonstrated that retinoic acid treatment consistently increased the expression of RARE-TK-luc which contains two tandem repeats of the retinoic acid responsive element from the β-retinoic acid receptor gene linked to the thymidine kinase promoter (FIG. 8B). Furthermore, retinoic acid treatment did not significantly affect the expression of luciferase fusion genes containing the cytomegalovirus promoter or the thymidine kinase promoter.

Example 11
Concentration Dependence of Retinoic Acid Mediated Repression

Figure 9:
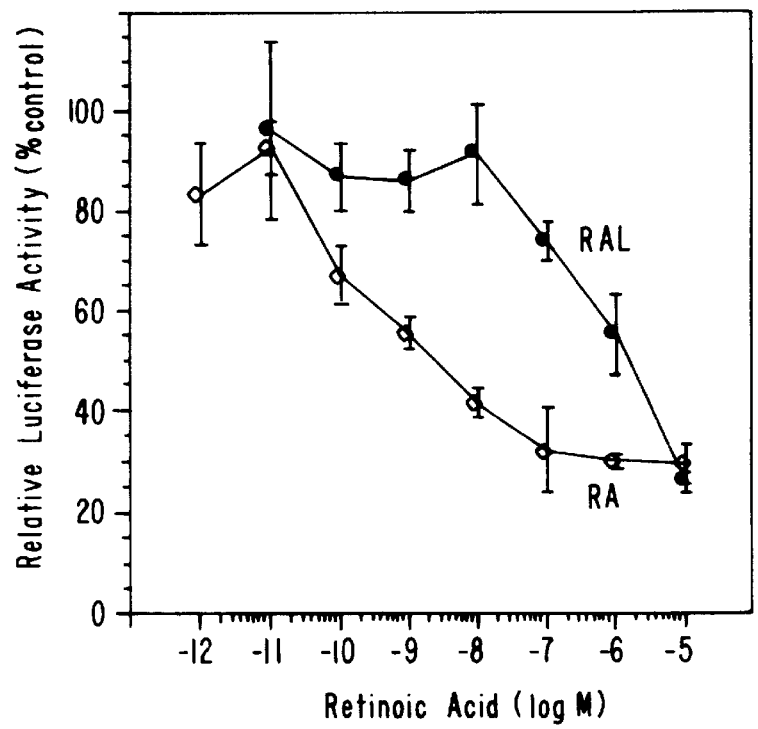
FIG. 9 presents the dose dependence of retinoic acid on the repression of a reporter gene under the control of the CT/CGRP upstream regulatory region. The CAL1125-luc fusion gene was transfected into CA77 cells and treated with various concentrations of either retinoic acid (RA), retinal (RAL), or the ethanol vehicle as the control. The luciferase activities from retinoic acid treatments (mean and standard deviation of two experiments) and from retinal treatments (mean and standard deviation of duplicate plates from one experiment) were normalized relative to control cells. The luciferase activities of all control plates were at least 125, 000 light units/50 µg protein extract.

The retinoic acid concentrations required for repression of the CT/CGRP promoter were measured by transfection of the 1125 CAL-luc reporter gene into the CA77 cells. 100 nM retinoic acid produced the maximal amount of repression, a 3-fold decrease of control activity. The amount of retinoic acid required for half-maximal repression was about 0.2 nM (FIG. 9). This measurement correlates well with previous measurements of the nuclear retinoic acid receptor (RAR) binding affmities ($K_d$ 0.2 nM; Yang, N., R. Schule, D. J. Mangelsdorf, and R. M. Evans. (1991) *Proc. Natl. Acad. Sci. USA* 88, 3559–3563), suggesting that retinoic acid is working through RARs, rather than αRXR, which requires at least 10-fold greater levels of retinoic acid for activation (Mangelsdorf, D. J., E. S. Ong, J. A. Dyck, and R. M. Evans. (1990) *Nature* 345, 224–229). Retinal, a related retinoid that has lower affinity for the retinoic acid receptors (Giguere, V., E. S. Ong, S. Prudimar, and R. M. Evans. (1987) *Nature* 330, 624–629; Petkovich, M., N. J. Brand, A. Krust, and P. Chambon. (1987) *Nature* 330, 444–450), only repressed the CT/CGRP promoter activity at concentrations of 0.100 µM or greater and was half-maximal at 0.3 µM retinal (FIG. 9).

Figure 10A:
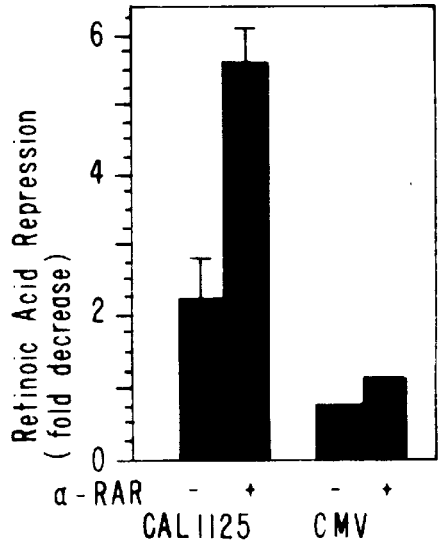
FIGS. 10A and 10B show the effect of cotransfection with the α-Retinoic Acid Receptor on retinoic acid mediated regulation of transcription.
Figure 10B:
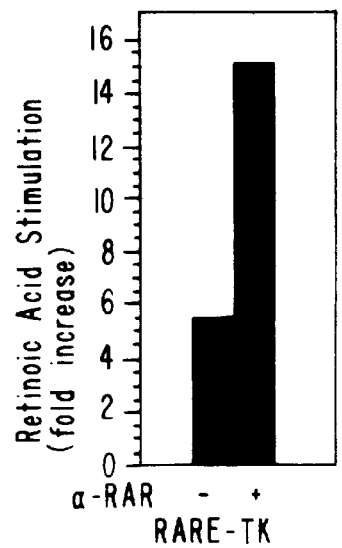

Example 12
Effect of Cotransfection of Retinoic Acid Receptor Gene on Retinoic Acid Mediated Repression Since retinoic acid mediated repression of CT/CGRP promoter activity appears to act through an RAR, α-RAR was assayed for its ability to increase repression of the promoter activity in CA77 cells. Cotransfection of α-RAR elicited a 5-fold retinoic acid dependent repression in CAL1125-luc activity in CA77 cells , as compared to a 2-fold repression of parallel cultures without cotransfected receptor (FIG. 10). Cotransfection of the α-RAR expression vector caused a 15-fold retinoic acid dependent stimulation of RARE-TK-luc activity, which is 3-fold greater than the stimulation observed in the absence of cotransfected receptor. Receptor cotransfection did not significantly affect CMV-luc activity. Furthermore, cotransfection of α-RXR alone had no effect relative to control, and cotransfection of both α-RXR and α-RAR does not increase repression over that seen with α-RAR alone (FIG. 10). These results support the involvement of the receptors and, furhermore, suggest that RAR levels may be a limiting factor in retinoic acid repression in the CA77 cells.

Example 13
Cell Specificity of Retinoic Acid Repression

The experiment described in Example 12 was repeated in the 44-2C and HeLa cell lines. In the 44-2C cell line, retinoic acid caused a 2-fold repression of 1 125-920-TK-luc activity (FIG. 11A). Cotransfection with the α-RAR expression vector did not appear to increase repression in the 44-2C cells. As controls, RARE-TK-luc increased activity 35-fold showing that retinoic acid could stimulate transcription in the 44-2C cells while TK-luc had no effect on activity, indicating the specificity of the retinoic acid effects (FIG. 11A).

In HeLa cells, the 1125-920 bp enhancer increased TK promoter activity 5–6-fold; however, retinoic acid had no effect on 1125-920-TK-luc activity (FIG. 11B). Repression was not observed even with cotransfection of α-RAR, α-RXR or both α-RAR and α-RXR. It is noteworthy that even the enhanced expression caused by the presence of the 1125-920 bp element was not repressed by retinoic acid treatment. These results establish that retinoic acid repression requires the presence of cell-specific proteins.

Example 14
Retinoic Acid Receptor Binding to the CT/CGRP Enhancer Element

Figure 12:
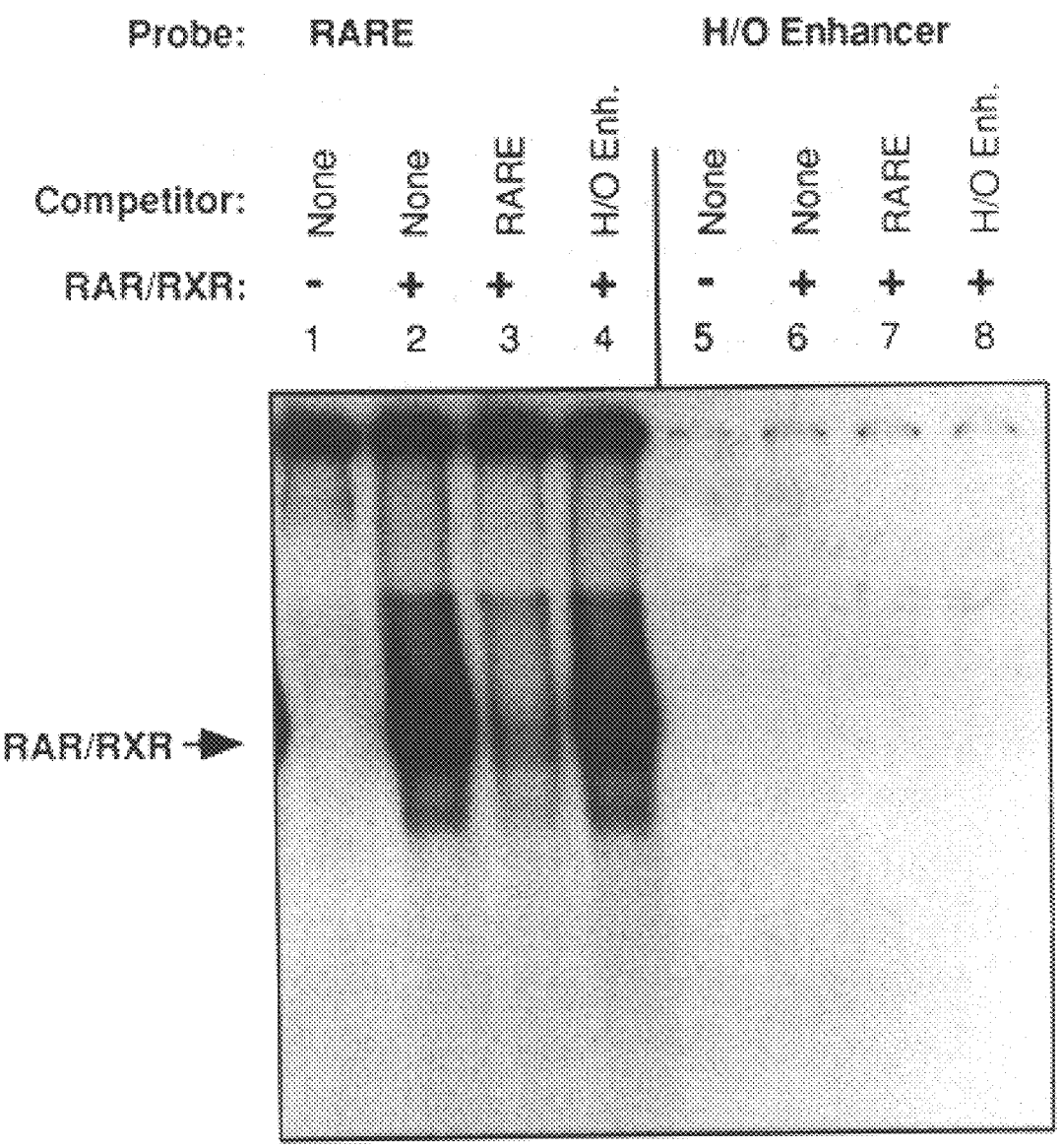
FIG. 12 presents competition assays which tested binding of RAR-RXR to the CT/CGRP enhancer. Approximately 0.5 μg each of GST-RAR and GST-RXR fusion proteins were mixed, then added to a binding reaction containing either RARE probe (lanes 2–4) or CT/CGRP enhancer probe (lanes 6–8). Control lanes contain binding reactions without RAR-RXR with either RARE probe (lane 1) or CT/CGRP enhancer (lane 4). 100-fold excess unlabeled competitor RARE or H/O enhancer DNA was added to reactions containing RARE (lanes 3, 4) or H/O enhancer probe (lanes 5, 6). The gel was exposed to film for 16 hr without an intensifying screen. Longer exposures did not reveal any clear binding to the CT/CGRP probe.

Binding of the RARs to the 18 bp CT/CGRP enhancer was tested by electrophoretic mobility shift assay. Radiolabeled CT/CGRP enhancer oligonucleotide was incubated with bacterial synthesized fusion proteins containing RAR and RXR linked to glutathione-S-transferase (GST). The GST-RAR/RXR protein did not observably bind to the CT/CGRP enhancer (FIG. 12). As a positive control, a binding assay with the RARE fragment demonstrated that a complex containing the radiolabeled RARE oligonucleotides and GST-RARARX protein could be easily detected.

Competition experiments showed that addition of excess unlabeled competitor RARE oligonucleotides caused a marked reduction in the receptor complex. However, as expected, addition of a 1 00-fold excess of unlabeled CT/CGRP oligonucleotide did not affect binding (data not shown). Consequently, the RAR/RXR protein has at least a 100-fold lower affinity for the CT/CGRP enhancer than a known RARE. One possible reason for the lack of binding to the CT/CGRP enhancer seen with bacterial synthesized RAR and RXR proteins is that RAR binding might require a cellular protein other than RXR.

To test the requirement for cell specific factors, a competition binding assay was performed using CA77 nuclear extracts. A RARE DNA-RAR protein complex was identified by competition with either a 10-fold excess of unlabeled RARE DNA or the palindromic thyroid hormone response element DNA (TRE-pal; data not shown). TRE-pal binds retinoic acid receptors, yet has a very different sequence than the direct repeats that constitute the RARE probe. A second, apparently nonspecific, complex was not fuilly competed even with 50-fold excess competitors. In contrast to competition with the RARE and TRE-pal oligonucleotides, even up to a 500- fold excess of the CT/CGRP enhancer oligo-nucleotide did not compete away the RARE DNA-receptor. These results agree with the lack of binding seen with bacterial synthesized receptors.

Example 15
Effect of Retinoic Acid on CT/CGRP Factor Binding

Figure 13:
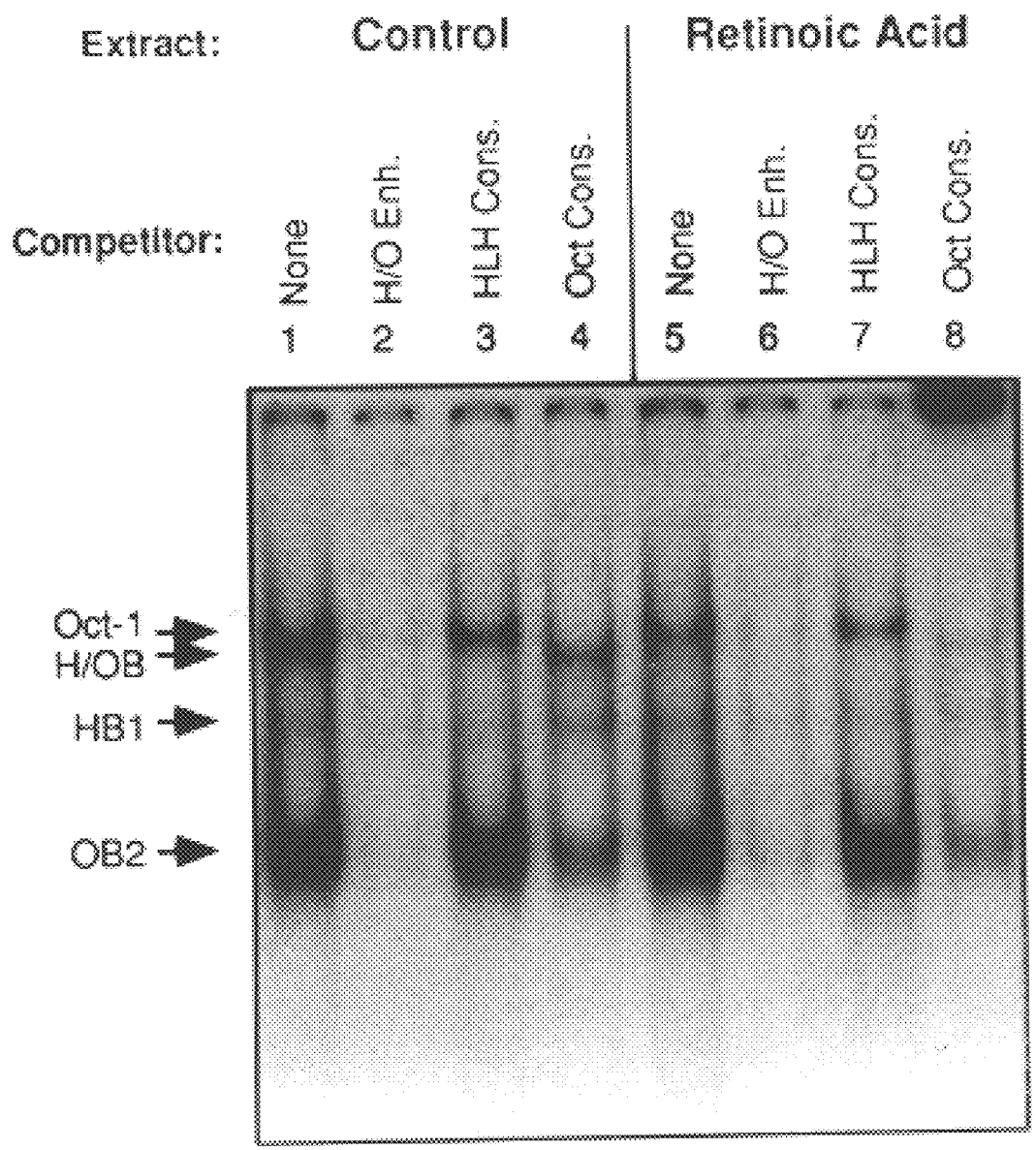
FIG. 13 shows electrophoretic mobility shift assays which tested binding of the HLH and Oct factors in nuclear extracts from retinoic acid treated CA77 cells. A mobility shift assay was done using equal amounts of nuclear extract (6 μg) prepared from CA77 cells treated with the ethanol vehicle (lanes 1–4) or retinoic acid (lanes 5–8). The extracts were preincubated before addition of the CT/CGRP enhancer probe either without competitor oligonucleotide (lanes 1, 5), or with 50-fold excess of competitor oligonucleotides, including the self-competitor (lanes 2, 6), consensus HLH motif (lanes 3, 7), or consensus octamer motif (lanes 4, 8).

The effect of retinoic acid treatment on the binding of the HLH and octamer proteins in CA77 nuclear extracts to the CT/CGRP enhancer was tested with electrophoretic mobility shift assays. The assays were performed with nuclear extracts prepared from CA77 cells treated for 24 hours with either retinoic acid or the ethanol vehicle. The only detectable difference was a relative diminishment of the H/OB complex (FIG. 13). Densitometric scans indicated that there was about a 2-fold decrease in H/OB, but no significant change in OB2, HB1, or Oct-1, in the nuclear extracts from retinoic acid treated cells.

Figure 14:
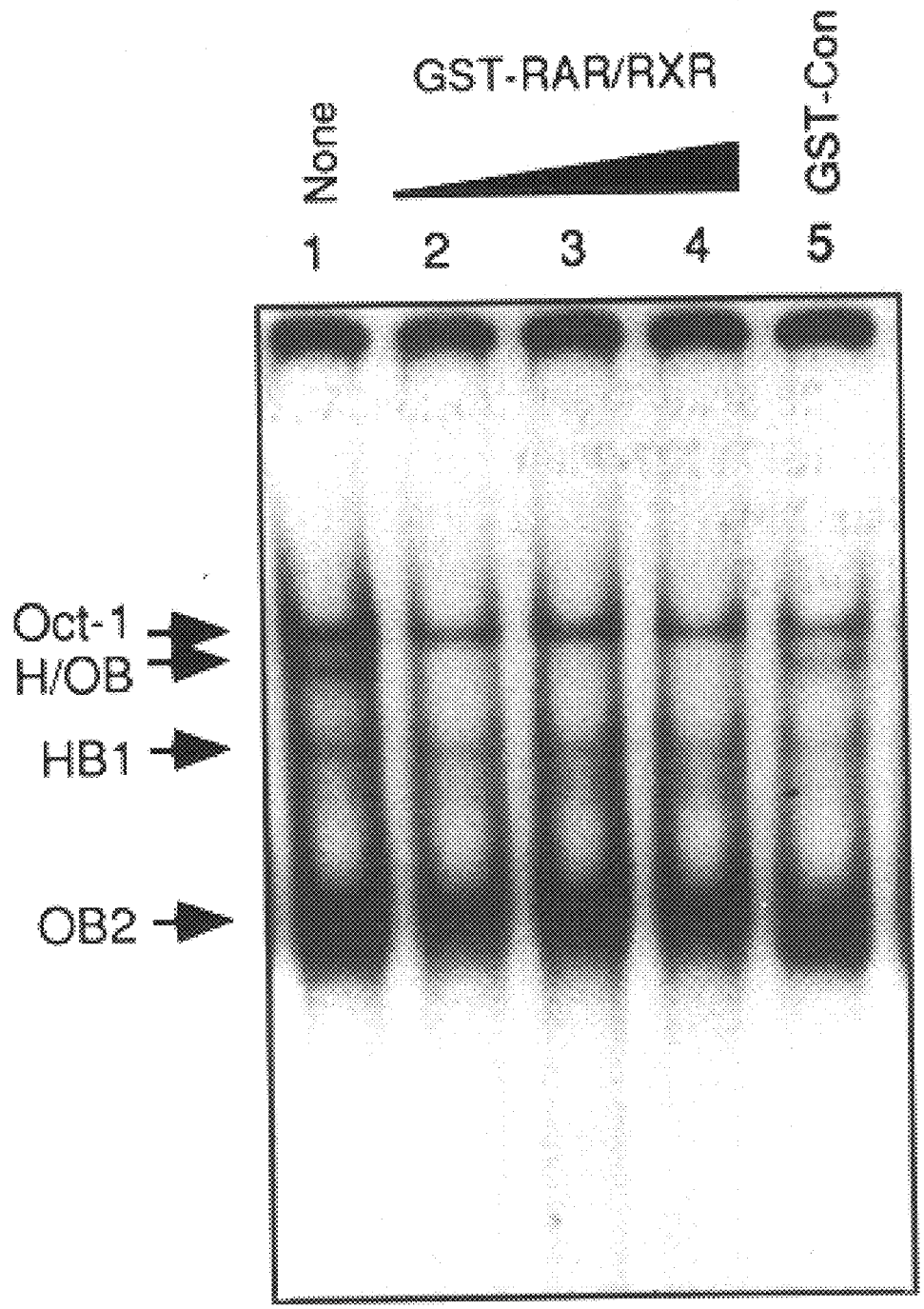
FIG. 14 shows the effects of RAR/RXR on complex formation in CA77 nuclear extracts. Mobility shift assays contained 4 μg CA77 extract with the CT/CGRP enhancer probe. Binding assays were incubated without RAR/RXR (lane 1) or pre-incubated with approximately 0.05, 0.125 or 0.25 μg RAR/RXR hybrid complexes (lanes 2–5). As a negative control, a control GST fusion protein (0.5 μg) was incubated in the binding reaction (lane 6).

GST-RAR/RXR proteins were added to the CA77 nuclear extract binding reaction to determine whether the retinoic acid receptors were directly interfering with H/OB complex formation (FIG. 14). Addition of RAR-RXR caused a nearly complete loss of the H/OB complex. In contrast, there was no detectable effect on the level of the Oct-1 or HB1 CT/CGRP enhancer complexes. A slight reduction in the mobility of the OB2 complex was observed which might indicate an interaction between receptors and OB2 (FIG. 14). It should be noted that at high concentrations (0.25 μg or greater) both the RAR and RXR homodimers also specifically removed the H/OB complex, but at lower concentrations (0.05 μg), only the RAR homodimer and the RAR/RXR heterodimer were effective. These data demonstrate that retinoic acid repression is mediated through RAR. As a control for any effect the GST moiety might have on the binding reaction, a GST-fusion protein containing a non-DNA binding protein did not selectively reduce the H/OB complex, even at 10 times the amount of receptor protein.

These results confirm the observations made with the retinoic acid treated extracts and suggest that the loss of the HLH-octamer complex is directly caused by the retinoic acid receptor protein.

To further support the specificity of RAR interference with the H/OB complex, the GST-RAR-RXR proteins were added to a HeLa nuclear extract binding reaction As expected, two prominent complexes containing Oct-1 and an HLH protein were seen. In addition, a very faint third complex was seen to co-migrate with the OB2 complex of CA77 nuclear extracts (data not shown). Addition of RAR and RXR homodimers, RAR-RXR heterodimer, or the GST control fusion protein did not have any effect on the Oct-1 or HLH complexes as seen with the CA77 extracts. Interestingly, RAR homodimer and the RAR/RXR heterodimer, but no RXR homodimers, did compete the faint complex that comigrated with OB2. Preliminary characterization suggests that this complex belongs to the octamer protein family although it remains to be determined whether it represents a small amount of OB2. The selective interference of RAR homodimer and RAR/RXR heterodimer supports the data that RAR and RAR/RR specifically interrupts the H/OB complex seen with CA77 nuclear extracts.

EQUIVALENTS

Those skilled in the art will recognize, or be able to ascertain using no more than routine experimentation, numerous equivalents to the specific embodiments described herein. Such equivalents are considered to be within the scope of this invention and are covered by the following claims.

---

What is claimed is:

1. A method for regulating gene expression, comprising:
selecting a gene of interest for regulated expression;
constructing a DNA sequence containing the gene of interest and an
enhancer element of the CT/CGRP gene forming a DNA construct, said enhancer element consisting of the nucleotide sequence of SEQ ID NO:1 or a functional homolog thereof;
inserting the DNA construct into a recombinant expression vector; and
introducing the recombinant expression vector into a host cell under
conditions such that the expression of the gene of interest is regulated.

2. The method of claim 1 wherein the gene of interest is calcitonin.

3. The method of claim 1 wherein the host cell is exposed to a member of the superfamily of steroids and retinoids.

4. The method of claim 1 wherein the host cell is neuroendocrine derived.

5. The method of claim 1 wherein the host cell is selected such that the expression of the gene of interest is repressed by a member of the superfamily of steroids and retinoids.

6. The method of claim 5 wherein the host cell is neuroendocrine derived.

7. The method of claim 5 wherein the host cell is exposed to glucocorticoids.

8. The method of claim 5 wherein the host cell is exposed to retinoic acid.

9. The method of claim 7 wherein the host cell is exposed to dexamethasone.

10. The method of claim 8 wherein the host cell is a 44-2C cell.

11. The method of claim 8 wherein the host cell is a CA77 cell.

12. The method of claim 9 wherein the host cell is a 44-2C ell.

13. An in vitro method for regulating gene expression, comprising:
selecting a gene of interest for regulated expression;
constructing a DNA sequence containing the gene of interest and an enhancer element of the CT/CGRP gene forming a DNA construct, said enhancer element consisting of the nucleotide sequence of SEQ ID NO:1 or a functional homolog thereof;
inserting the DNA construct into a recombinant expression vector; and
introducing the recombinant expression vector into a host cell under in vitro conditions such that the expression of the gene of interest is regulated.

14. The method of claim 13 wherein the gene of interest is calcitonin.

15. The method of claim 13 wherein the host cell is exposed to a member of the superfamily of steroids and retinoids.

16. The method of claim 13 wherein the host cell is neuroendocrine derived.

17. The method of claim 13 wherein the host cell is selected such that the expression of the gene of interest is repressed by a member of the superfamily of steroids and retinoids.

18. The method of claim 13 wherein the host cell is exposed to glucocorticoids.

* * * * *